United States Patent
Nandwana et al.

(10) Patent No.: US 11,591,223 B2
(45) Date of Patent: Feb. 28, 2023

(54) NANOCOMPOSITES, NANOCOMPOSITE SENSORS AND RELATED METHODS

(71) Applicant: Northwestern University, Evanston, IL (US)

(72) Inventors: Vikas Nandwana, Evanston, IL (US); Vinayak P. Dravid, Glenview, IL (US)

(73) Assignee: Northwestern University, Evanston, IL (US)

(*) Notice: Subject to any disclaimer, the term of this patent is extended or adjusted under 35 U.S.C. 154(b) by 362 days.

(21) Appl. No.: 16/638,548

(22) PCT Filed: Aug. 14, 2018

(86) PCT No.: PCT/US2018/046674
§ 371 (c)(1),
(2) Date: Feb. 12, 2020

(87) PCT Pub. No.: WO2019/036451
PCT Pub. Date: Feb. 21, 2019

(65) Prior Publication Data
US 2021/0107792 A1  Apr. 15, 2021

Related U.S. Application Data

(60) Provisional application No. 62/545,686, filed on Aug. 15, 2017.

(51) Int. Cl.
*C01B 32/19* (2017.01)
*C01G 39/06* (2006.01)
(Continued)

(52) U.S. Cl.
CPC ............ *C01B 32/19* (2017.08); *C01B 19/007* (2013.01); *C01G 39/06* (2013.01); *C01G 49/08* (2013.01);
(Continued)

(58) Field of Classification Search
CPC ....... C01B 32/19; C01B 19/007; C01G 39/06; C01G 49/08; C12N 9/0006; G01N 21/77;
(Continued)

(56) References Cited

U.S. PATENT DOCUMENTS

| 9,911,974 B2 | 3/2018 | de Guzman et al. |
| 2003/0224168 A1 | 12/2003 | Mack et al. |

(Continued)

FOREIGN PATENT DOCUMENTS

| CN | 103965835 A | 8/2014 |
| WO | WO 2012/155196 A1 | 11/2012 |

OTHER PUBLICATIONS

Ahmad, et al., Functionalized Molybdenum Disulfide Nanosheets for 0D-2D Hybrid Nanostructures: Photoinduced Charge Transfer and Enhanced Photoresponse, J. Phys. Chem. Lett, 2017; 8: 1729-1738 (Year: 2017).*

(Continued)

*Primary Examiner* — Daniel C. McCracken
(74) *Attorney, Agent, or Firm* — Bell & Manning, LLC

(57) ABSTRACT

Methods for making nanocomposites are provided. In an embodiment, such a method comprises combining a first type of nanostructure with a bulk material in water or an aqueous solution, the first type of nanostructure functionalized with a functional group capable of undergoing van der Waals interactions with the bulk material, whereby the first type of nanostructure induces exfoliation of the bulk material to provide a second, different type of nanostructure while inducing association between the first and second types of nanostructures to form the nanocomposite.

15 Claims, 21 Drawing Sheets

(51) Int. Cl.

| | |
|---|---|
| *C01G 49/08* | (2006.01) |
| *C12N 9/04* | (2006.01) |
| *G01N 21/77* | (2006.01) |
| *C01B 19/00* | (2006.01) |
| *B82Y 15/00* | (2011.01) |
| *B82Y 40/00* | (2011.01) |
| *B82Y 30/00* | (2011.01) |

(52) U.S. Cl.
CPC ............ *C12N 9/0006* (2013.01); *G01N 21/77* (2013.01); *B82Y 15/00* (2013.01); *B82Y 30/00* (2013.01); *B82Y 40/00* (2013.01); *C01P 2004/64* (2013.01); *C01P 2004/80* (2013.01); *C12Y 101/03004* (2013.01); *G01N 2021/7756* (2013.01)

(58) Field of Classification Search
CPC ............ G01N 2021/7756; B82Y 15/00; B82Y 30/00; B82Y 40/00; C01P 2004/64; C01P 2004/80; C01P 2002/82; C01P 2002/85; C01P 2004/04; C01P 2004/16; C01P 2004/24; C12Y 101/03004
See application file for complete search history.

(56) References Cited

U.S. PATENT DOCUMENTS

| | | |
|---|---|---|
| 2004/0108276 A1 | 6/2004 | Christodoulou |
| 2012/0267234 A1* | 10/2012 | Reece ................. C01B 3/042 977/773 |
| 2013/0284968 A1 | 10/2013 | Azizov et al. |
| 2016/0204416 A1 | 7/2016 | Wu et al. |
| 2016/0243523 A1 | 8/2016 | Saini et al. |
| 2018/0208734 A1 | 7/2018 | Ozkan et al. |
| 2018/0241032 A1 | 8/2018 | Pan et al. |

OTHER PUBLICATIONS

Joensen, et al., Single-layer MoS2, Mat. Res. Bull. 1986; 21: 457-461 (Year: 1986).*
Andrea C. Ferrari, "Raman spectroscopy of graphene and graphite: Disorder, electron-phonon coupling doping and nonadiabatic effects," Solid State Communications, vol. 143, Apr. 27, 2007, pp. 47-57.
Zhou et al. "Graphene-Wrapped Fe3O4 Anode Material with Improved Reversible Capacity and Cyclic Stability for Lithium Ion Batteries," Chemistry of Materials, vol. 22, No. 18, Aug. 26, 2010, pp. 5306-5313.
The International Search Report and Written Opinion issued in International Patent Application No. PCT/US18/46674 dated Jan. 11, 2019, pp. 1-11.
Liu et al., "Iron Oxide Decorated $MoS_2$ Nanosheets with Double PEGylation for Chelator-Free Radiolabeling and Multimodal Imaging Guided Photothermal Therapy," ACS Nano 2015, vol. 9, No. 1, pp. 950-960.
Nandwana et al., "One-Pot Green Synthesis of $Fe_3O_4$/$MoS_2$ 0D/2D Nanocomposites and Their Application in Noninvasive Point-of-Care Glucose Diagnostics," *ACS Appl. Nano Mater.* 2018, vol. 1, pp. 194901958.
Peng et al., "Ultrathin Two-Dimensional $MnO_2$/Graphene Hybrid Nanostructures for High-Performance, Flexible Planar Supercapacitors," Nano Letters 2013, vol. 13, pp. 2151-2157.
Peng et al., Supporting Information for "Ultrathin Two-Dimensional MnO2/Graphene Hybrid Nanostructures for High-Performance, Flexible Planar Supercapacitors," 2013, pp. 1-11.
Wang et al., "Biosensor Based on Ultrasmall $MoS_2$ Nanoparticles for Electrochemical Detection of $H_2O_2$ Released by Cells at the Nanomolar Level," Anal. Chem. 2013, vol. 85, pp. 10289-10295.
Yu et al., "Smart $MoS_2$/ $Fe_3O_4$ Nanotheranostic for Magnetically Targeted Photothermal Therapy Guided by Magnetic Resonance/ Photoacoustic Imaging," Theranostics 2015, vol. 5, Issue 9, pp. 931-945.
Joensen et al., "Single-Layer $MoS_2$, " Mat. Res. Bull. 1986, vol. 21, pp. 457-461.
Zhu et al., "Fast Li Storage in $MoS_2$-Graphene-Carbon Nanotube Nanocomposites : Advantageous Functional Integration of 0d, 1D, and 2D Nanostructures," Adv. Energy Mater. 2015, vol. 5, pp. 1401170-1401177.
V. Nicolos et al., "Liquid Exfoliation of Layered Materials," Science Jun. 21, 2013, vol. 340, pp. 1226419-1-1226419-18.
D. Yang et al., "Li-Intercalation and Exfoliation of WS2," J. Phys. Chem. Solids 1996, vol. 57, Nos. 6-8, pp. 1113-1116.
Kufer et al., "Hybrid 2D-0D $MoS_2$-PbS Quantum Dot Photodetectors, " Adv. Mater. 2015, vol. 27, pp. 176-180.
Q. Qu et al., "2D Sandwich-like Sheets of Iron Oxide Grown on Graphene as High Energy Anode Material for Supercapacitors," Adv. Mater. 2011, vol. 23, pp. 5574-5580.
Jonathan N. Coleman, "Liquid Exfoliation of Defect-Free Graphene," Accounts of Chemical Research 2013, vol. 46, No. 1, pp. 14-22.
Ahmad et al., "Functionalized Molybdenum Disulfide Nanosheets for 0D-2D Hybrid Nanostructures: Photoinduced Charge Transfer and Enhanced Photoresponse," J. Phys. Chem. Lett. 2017, vol. 8, pp. 1729-1738.
Sandoval et al., "Raman study and lattice dynamics of single molecular layers of $MoS_2$," The American Physical Society Physical Review B Aug. 15, 1991-II, vol. 44, No. 8, pp. 3955-3962.
Smith et al., "Large-Scale Exfoliation of Inorganic Layered Compounds in Aqueous Surfactant Solutions," Adv. Mater. 2011, vol. 23, pp. 3944-3948.
Chou et al., "Ligand Conjugation of Chemically Exfoliated $MoS_2$," J. Am. Chem. Soc. 2013, vol. 135, pp. 4584-4587.

* cited by examiner

NANOCOMPOSITES, NANOCOMPOSITE SENSORS AND RELATED METHODS

CROSS-REFERENCE TO RELATED APPLICATIONS

This application is a National Stage of International Application No. PCT/US2018/046674, filed Aug. 14, 2018, which claims the benefit of U.S. Patent Application No. 62/545,686, filed Aug. 15, 2017, the contents of each of which are herein incorporated by reference.

REFERENCE TO GOVERNMENT RIGHTS

This invention was made with government support under DMR1507810 awarded by the National Science Foundation. The government has certain rights in the invention.

BACKGROUND

Two-dimensional (2D) nanomaterials have drawn tremendous interest due to their unique structural and electronic properties.[1-4] Nanocomposites with 2D nanomaterials as a host matrix have demonstrated enhanced mechanical, thermal, and catalytic properties for a range of applications including optoelectronics, catalysis, energy, and biomedicine.[5-9] Regarding biomedicine however, the existing technology for glucose detection is based on an electrochemical method. It requires a glucose test strip and a device called glucometer that is powered by a battery. The patient has to prick blood from his/her finger and transfer onto test strip which is inserted in glucometer which gives a reading of blood glucose level. The test is invasive and blood pricking is inconvenient for many patients, especially elderly people and kids.

SUMMARY

Nanocomposites, methods for making the nanocomposites, and methods for using the nanocomposites, e.g., for $H_2O_2$ sensing and non-invasive glucose sensing, are provided.

In one aspect, methods for making nanocomposites are provided. In an embodiment, such a method comprises combining a first type of nanostructure with a bulk material in water or an aqueous solution, the first type of nanostructure functionalized with a functional group capable of undergoing van der Waals interactions with the bulk material, whereby the first type of nanostructure induces exfoliation of the bulk material to provide a second, different type of nanostructure while inducing association between the first and second types of nanostructures to form the nanocomposite.

In another aspect, sensors for a target analyte are provided. In an embodiment, such a sensor comprises a nanocomposite comprising a plurality of a first type of nanostructures and a plurality of a second type of nanostructures, the first type of nanostructures in association with the second type of nanostructure, wherein the nanocomposite exhibits intrinsic catalytic activity in a reaction involving a target analyte; and a chromogenic material capable of exhibiting a color change in the presence of the target analyte.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

DETAILED DESCRIPTION

Figure 1A:
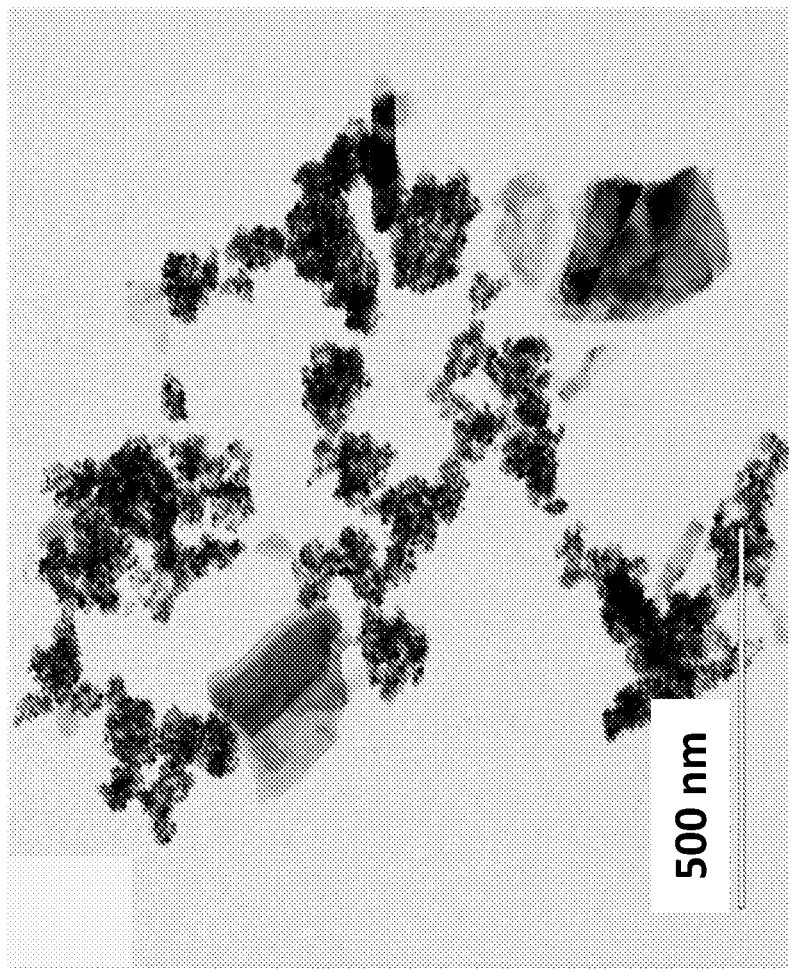
FIG. 1A depicts a TEM image of $MoS_2/Fe_3O_4$ nanocomposite.

Nanocomposites, methods for making the nanocomposites, and methods for using the nanocomposites, e.g., for $H_2O_2$ sensing and non-invasive glucose sensing, are provided.

In one aspect, a nanocomposite comprising at least two different types of nanostructured materials is provided. By "different type" it is meant that the two nanostructured materials have different chemical compositions, different morphologies, or both. In embodiments, one of the nanostructured materials is composed of a plurality of zero-dimensional (0D) nanostructures. By "zero-dimensional" it is meant a nanostructure having each of its three dimensions on the order of about 100 nm or less. The three dimensions may also be of similar magnitude, e.g., the height, width and thickness of the nanostructure, are similar, e.g., within ±20%, ±10%, ±5%, etc. of each other. A nanoparticle is an illustrative example of a 0D nanostructure. The nanoparticles may be spherical, but this term encompasses irregularly shaped particles which are still reasonably well defined by a sphere. (See FIG. 1A.) The nanoparticles may be characterized by an average diameter. The average diameter may be about 100 nm or less, about 50 nm or less, about 25 nm or less, about 10 nm or less, or in the range of from about 1 nm to about 100 nm.

In embodiments, one of the nanostructured materials is composed of a plurality of one-dimensional (1D) nanostructures. By "one-dimensional" it is meant a nanostructure having at least two dimensions on the order of about 100 nm or less. The two dimensions may also be of similar magnitude to each other as described above. The other dimension may be substantially greater, e.g., about 25 times greater, about 50 times greater, about 100 times greater, about 200 times greater, etc. A nanowire is an illustrative example of a 1D nanostructure. Other illustrative examples include nanorods, nanofibers, nanowhiskers. The 1D nanostructures may characterized by an average diameter. The average diameter may be about 25 nm or less, about 10 nm or less, about 5 nm or less, or about 1 nm or less. The other dimension of the 1D nanostructure, e.g., the length, is not particularly limited, but as described above, is substantially greater than the diameter. The term "diameter" is not meant to imply that the 1D nanostructures are limited to circular cross-sections. Other cross-sections, e.g., square, rectangle, ellipse, etc. may be used, in which case "diameter" may refer to a width, height, major diameter, etc.

In embodiments, one of the nanostructured materials is composed of a plurality of two-dimensional (2D) nanostructures. By "two-dimensional" it is meant a nanostructure having at least one dimension on the order of about 100 nm or less. The other two dimensions may be substantially greater, e.g., about 25 times greater, about 50 times greater, about 100 times greater, about 200 times greater, etc. These other two dimensions may also be of similar magnitude to each other as described above. A nanosheet is an illustrative example of a 2D nanostructure. The nanosheets may characterized by an average thickness. The average thickness may be about 25 nm or less, about 10 nm or less, about 5 nm or less, or about 1 nm or less. The other dimensions of the nanosheets, e.g., the length and width, are not particularly limited, but as described above, are substantially greater than the thickness. The terms "length" and "width" are not meant to imply that the nanosheets are limited to square or rectangular shapes. Other shapes, including irregular shapes may be used. (See FIG. 1A.) The nanosheet may be composed of one to a few (e.g., 3) atomic or molecular layers of the element/molecule from which the nanosheet is composed. Thus, the thickness of the nanosheet may be reported as the number of atomic/molecular layers in the nanosheet.

The term "average" refers to an average value over a representative number of nanostructures. Transmission electron microscopy (TEM) may be used to determine the size of the nanostructures. Raman spectroscopy may be used to determine the number of atomic/molecular layers in a nanosheet.

In the nanocomposite, the at least two different types of nanostructures are associated with each other, the association which is in the form of noncovalent, van der Waals interactions. The nature of the association (i.e., to confirm the van der Waals interactions) may be determined using Raman spectroscopy as described in the Example, below. To facilitate the association between the two different types of nanostructures in the nanocomposite, at least one of the nanostructures may be functionalized with functional groups. A variety of functional groups may be used, provided the functional group has an affinity (based on the capability of forming van der Waals interactions) for the material from which the other type of nanostructure is composed. Thus, the particular functional group selected will depend upon the chemical composition of the nanostructures. Illustrative functional groups include thiol, sulfate, carboxylate, cholate, sulfonate, and trimethyl ammonium. By way of illustration, thiol groups have a strong affinity towards chalcogenides (e.g., sulfides, selenides, tellurides). Thus, nanostructures functionalized with thiol groups may be used in order to facilitate association between the thiol-functionalized nanostructures and other nanostructures composed of a transition metal chalcogenide. Similarly sulfate, carboxylate, cholate, and sulfonate show strong affinity towards transition metals, thus nanostructures functionalized with these groups may be used to facilitate association with transition metal chalcogenides.

The functional groups may be provided by a variety of different types of molecules, e.g., 11-mercaptoundecanoic acid (MUA), oleic acid (OAc), sodium dodecyl sulfate (SDS), sodium cholate, sodium dodecyl benzene-sulfonate, and hexadecyltrimethylammonium bromide (CTAB).

A variety of materials may be used for the nanostructures of the nanocomposite, depending upon the desired application. Illustrative materials include noble metals (e.g., Au, Pt, Ag), quantum dots (CdS, CdSe, ZnSe, PbS, PbSe, PbTe, CdTe, InP, InAs, $Ag_2S$), graphene, transition metal chalcogenides (e.g., $MoS_2$, $MoTe_2$, $MoSe_2$, $WSe_2$, $WS_2$), transition metal oxides (e.g., $Fe_3O_4$, $Fe_2O_3$, MnO, ZnO, $MnFe_2O_4$, $ZnFe_2O_4$), and nitrides (e.g., BN).

The ratio (e.g., concentration ratio) of the at least two different types of nanostructures in the nanocomposite may be adjusted depending upon the desired application. By way of illustration, if the nanocomposite is used as a catalyst for a particular reaction, the ratio may be adjusted to maximize the rate of the reaction.

In embodiments, the nanocomposite comprises 0D nanoparticles and 2D nanosheets, wherein the 0D nanoparticles are distributed, e.g., uniformly, on the exposed surfaces of the 2D nanosheets. An illustrative nanocomposite comprising thiol-functionalized $Fe_3O_4$ 0D nanoparticles and $MoS_2$ 2D nanosheets is described in the Example below. (See also FIGS. 1A and 10.)

In another aspect, methods of making the nanocomposites are provided. In embodiments, the methods include combining a first type of nanostructure with a material from which a second type of nanostructure is composed, in water or an aqueous solution, whereby the first type of nanostructure induces exfoliation of the material to provide the second type of nanostructure and association between the first and second types of nanostructures to form the nanocomposite. The method may be carried out in the absence of any organic solvents. The use of functional groups on the first type of nanostructure facilitates the exfoliation of the material to provide the second type of nanostructure as well as association between the first and second types of nanostructures as described above. Thus, the methods achieve nanocomposites in a single step in which combining the first type of nanostructure with the material from which the second type of nanostructure is to be formed results in exfoliation to provide the second type of nanostructure as well as association between the first and second types of nanostructures. In other words, the exfoliation and association happen simultaneously, induced by the first type of nanostructure. However, sonication for a period of time may be used during the combining of the first and second types of nanostructures to further facilitate exfoliation and thus, association. The method may comprise additional steps, e.g., isolating the nanocomposite from unassociated nanostructures (e.g., via centrifuging and collecting a supernatant and dialyzing the supernatant).

In the paragraph immediately above and throughout the present disclosure, it is to be understood that the phrase "the material from which the second type of nanostructure is composed" (and the like) is meant to differentiate the "material" from the "second type of nanostructure." That is, the "material" and the "second type of nanostructure" are different physical entities. By way of example, a material may be bulk $MoS_2$, which is a solid layered material, and the second type of nanostructure may be individual nanosheets of $MoS_2$.

Similarly, it is to be understood that the material from which the second type of nanostructure is composed is not an intercalated material, e.g., is not an ion intercalated transition metal chalcogenide such as lithium ion intercalated $MoS_2$. Similarly, the material from which the second type of nanostructure is composed is not an exfoliated material, i.e., is not a material which has been subjected to an exfoliation technique such as exfoliated $MoS_2$.

The material from which the second type of nanostructure is composed is also generally unfunctionalized, i.e., free of other atoms or molecules (aside from the chemical compound making up the material).

Finally, in view of the description of "nanostructure" above, the first type of nanostructure is not a small molecule, a polymer molecule, a solvent molecule, or a surfactant molecule.

As an initial step, the method may include functionalizing the first type of nanostructure, e.g., by combining the first type of nanostructure with the functional group selected to have a strong affinity for the second type of nanostructure (or a molecule having the functional group). By "strong affinity" it is meant an affinity sufficiently high to achieve van der Waal interactions between the first and second types of nanostructures. Thus, also provided by the present disclosure is the functionalization method itself, e.g., combining a first type of nanostructure with a functional group having a strong affinity for a second type of nanostructure (or a molecule having the functional group). In the functionalization, the functional group may be covalently bound to the first type of nanostructure. The functional group is not necessarily directly covalently bound to the first type of nanostructure, i.e., when the functional group is provided by a molecule, the molecule may be covalently bound to the first type of nanostructure via another chemically appropriate functional group. This is illustrated by functionalizing $Fe_3O_4$ with 11-mercaptoundecanoic acid. The carboxylic acid group of 11-mercaptoundecanoic acid covalently bonds to $Fe_3O_4$ while the thiol group of the molecule is the functional group having a strong affinity for the second type of nanostructure.

Figure 10:
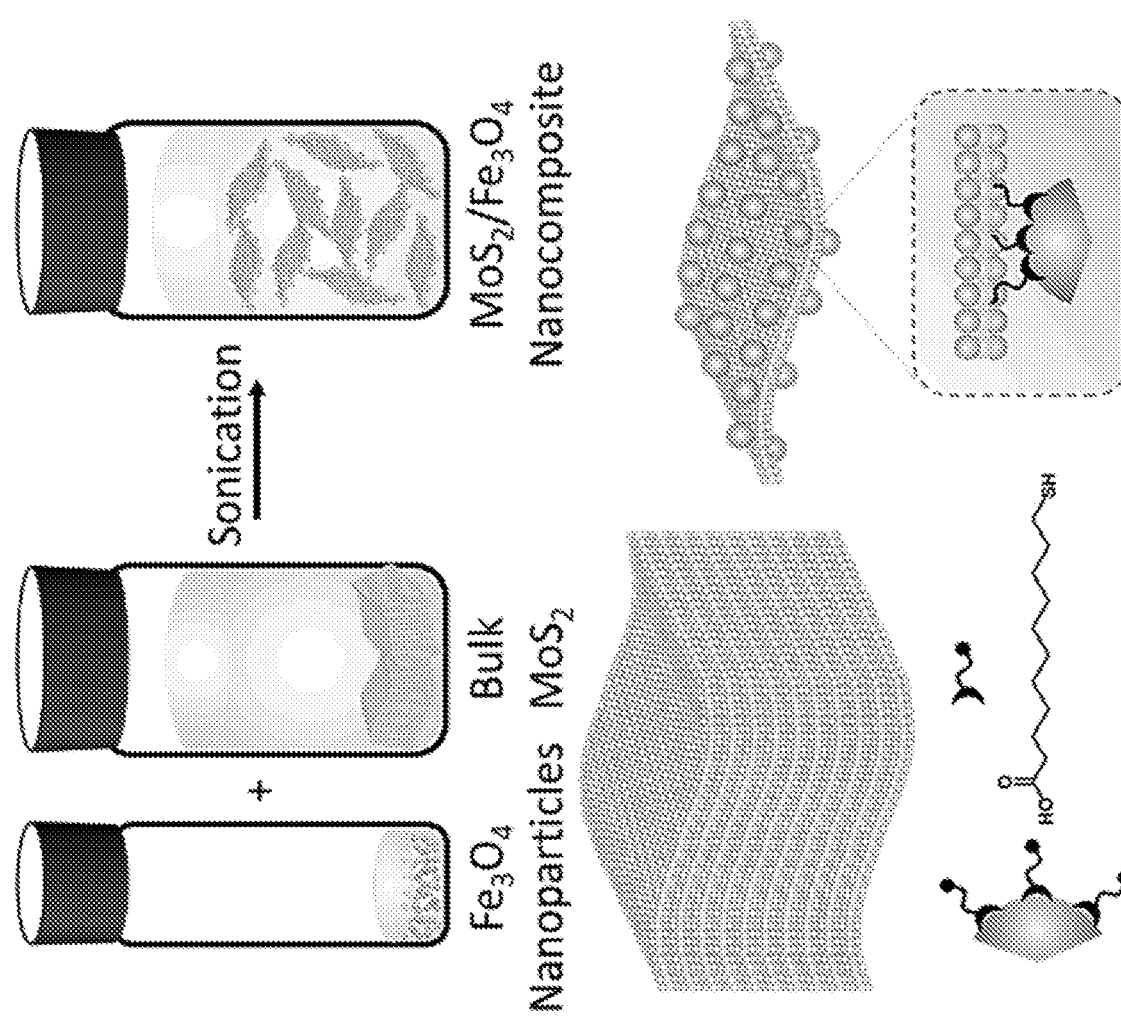
FIG. 10 depicts the synthesis of $MoS_2/Fe_3O_4$ nanocomposite via thiol functionalized $Fe_3O_4$ nanoparticles assisted by exfoliation of $MoS_2$.

An illustrative method for forming a 2D-$MoS_{2/0}$D-$Fe_3O_4$ nanocomposite is shown in FIG. 10 and is further described in the Example, below. As the Example shows, no surfactants or stabilizers are required to achieve the exfoliation of 2D-$MoS_2$. Moreover, the nanocomposite is formed in a single step in which the functionalized 0D-$Fe_3O_4$ nanoparticles ($Fe_3O_4$ nanoparticles functionalized with 11-mercaptoundecanoic acid) induce simultaneous exfoliation of bulk $MoS_2$ into 2D-$MoS_2$ nanosheets and association between the 0D-$Fe_3O_4$ nanoparticles and 2D-$MoS_2$ nanosheets to provide the nanocomposite.

By contrast, conventional methods of making 2D/0D nanocomposites include two steps. First, a bulk material is exfoliated (mechanically or chemically) to provide 2D nanostructures or the 2D nanostructures are grown (chemical vapor deposition). Then 0D nanoparticles are conjugated/grown onto the 2D nanostructures. As described above, the present methods can achieve the formation of 2D/0D nanocomposites in a single step. The present methods are also more flexible and may be applied to any combination of 0D and 2D nanostructures provided that the 0D nanostructures are functionalized with functional groups having a high affinity for the selected material for the 2D nanostructures. Since the method is based on surface functionality, instead of 0D nanostructures, 1D and 2D nanostructures with appropriate functional groups can also be used to exfoliate materials to provide 2D nanostructures and thus, 2D/1D and 2D/2D nanocomposites, respectively.

Depending upon the materials used for the nanostructures of the nanocomposites, the nanocomposites may exhibit intrinsic catalytic activity which may be exploited to provide a method for sensing a target analyte. Alternatively or in addition, the nanostructures of the nanocomposites may be further functionalized with receptors sensitive to a target analyte for use in a method for sensing the target analyte. Due to their high surface area and multiple functionalities, the nanocomposites may provide a higher limit of detection (LOD) for the target analyte. The type of intrinsic catalytic activity, receptors, and the target analytes are not particularly limited. Illustrative target analytes include biomarkers and toxic elements in fluids or air.

In embodiments, the nanocomposite exhibits intrinsic peroxidase activity, i.e., the ability to catalyze the oxidation of a substrate by hydrogen peroxide, $H_2O_2$. A chromogenic material capable of being oxidized by $H_2O_2$ may be used as the substrate. The color change induced by the oxidation may be detected by monitoring the absorbance of the chromogenic material at a particular wavelength of light. This wavelength may be one which overlaps with the absorbance spectrum of the oxidized chromogenic material, e.g., at or near an absorbance maximum. The absorbance is proportional to the concentration of $H_2O_2$. Illustrative chromogenic materials include 3,3',5,5'-Tetramethylbenzidine (TMB), o-Phenylenediamine (OPD), and 2,2'-azino-bis(3-ethylbenzothiazoline-6-sulphonic acid) (ABTS), p-nitrophenyl phosphate, 5 aminosalicylic acid, and 3,3' diaminobenzidine. The chromogenic material TMB turns blue when oxidized by $H_2O_2$; OPD turns orange when oxidized by $H_2O_2$; and ABTS turns green when oxidized by $H_2O_2$. (See FIGS. 4A and 4B.) The chromogenic material 5 aminosalicylic acid turns yellow when oxidized by $H_2O_2$; p-nitrophenyl phosphate turns yellow when oxidized by $H_2O_2$, and 3,3' diaminobenzidine turns brown when oxidized by $H_2O_2$.

The Example, below, demonstrates that an illustrative 2D-$MoS_2$/0D-$Fe_3O_4$ nanocomposite exhibits peroxidase activity and catalyzes the oxidation of TMB, OPD and ABTS by $H_2O_2$. Thus, such a nanocomposite may be used as a $H_2O_2$ sensor, by exposing the nanocomposite to a sample in the presence of a chromogenic material and measuring the absorbance of the chromogenic material. The sample is one which is suspected of containing the target analyte, $H_2O_2$. Quantitative determination of the concentration of $H_2O_2$ may be accomplished by comparing the measured absorbance to a calibration curve. (See FIG. 6B.) Rapid and accurate detection of $H_2O_2$ is useful in the fields of bioanalysis as well as food security and environmental protection.

Figure 7A:
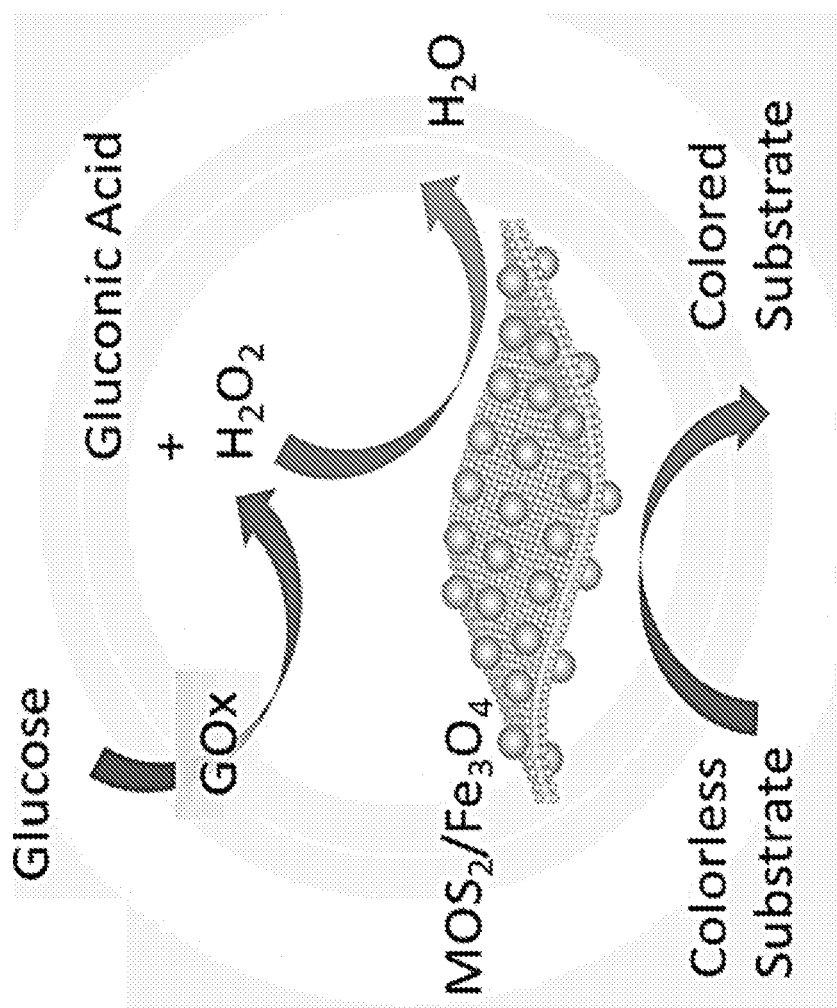
FIG. 7A illustrates the mechanism of glucose detection by the $MoS_2/Fe_3O_4$ nanocomposite.

Peroxidase activity may further be exploited to sense other target analytes besides $H_2O_2$. By way of illustration, since the oxidation of glucose by glucose oxidase (GOx) produces $H_2O_2$, nanocomposites exhibiting peroxidase activity may also be used to sense glucose. The mechanism is illustrated in FIG. 7A, for the illustrative 2D-$MoS_2$/0D-$Fe_3O_4$ nanocomposite. In this case, the nanocomposite is exposed to a sample suspected of containing glucose in the presence of a chromogenic material and GOx and the absorbance of the chromogenic material is measured. The sample may be a fluid (e.g., a bodily fluid such as saliva, blood, sweat, urine) from a subject (e.g., a mammalian subject). Since concentration of $H_2O_2$ is proportional to the concentration of glucose, the measured absorbance of the chromogenic material is proportional to the glucose concentration. Thus, quantitative determination of the concentration of glucose may be achieved. (See FIG. 7B.)

Other oxidoreductases besides GOx may be used, similar to the description above.

In embodiments, the nanocomposite, the chromogenic material, and the GOx (if present) may be in the form of an aqueous solution. However, in other embodiments, these materials may be deposited on a substrate. A variety of substrates may be used, including flexible substrates such as paper or plastics. Ink jet deposition may be used to deposit aqueous solutions of each of the materials on the substrate, e.g., in a layer-by-layer fashion. Next, the substrate may be exposed to the sample for a period of time. The exposed substrate may be heated for a period of time to facilitate drying. As described above, oxidation of the chromogenic material via $H_2O_2$ either present in the sample or produced due to glucose present in the sample, will induce a color change. The intensity of the resulting color (which may be visually detected) is proportional to the concentration of the $H_2O_2$/glucose in the sample. Qualitative and/or quantitative determination of the concentration may be achieved by comparing the intensity of the resulting color to a calibration color chart (i.e., a chart which associates a particular color/intensity with a particular analyte concentration). This embodiment is illustrated in FIG. 9 in the form of a non-invasive glucose diagnostic platform.

Figure 9:
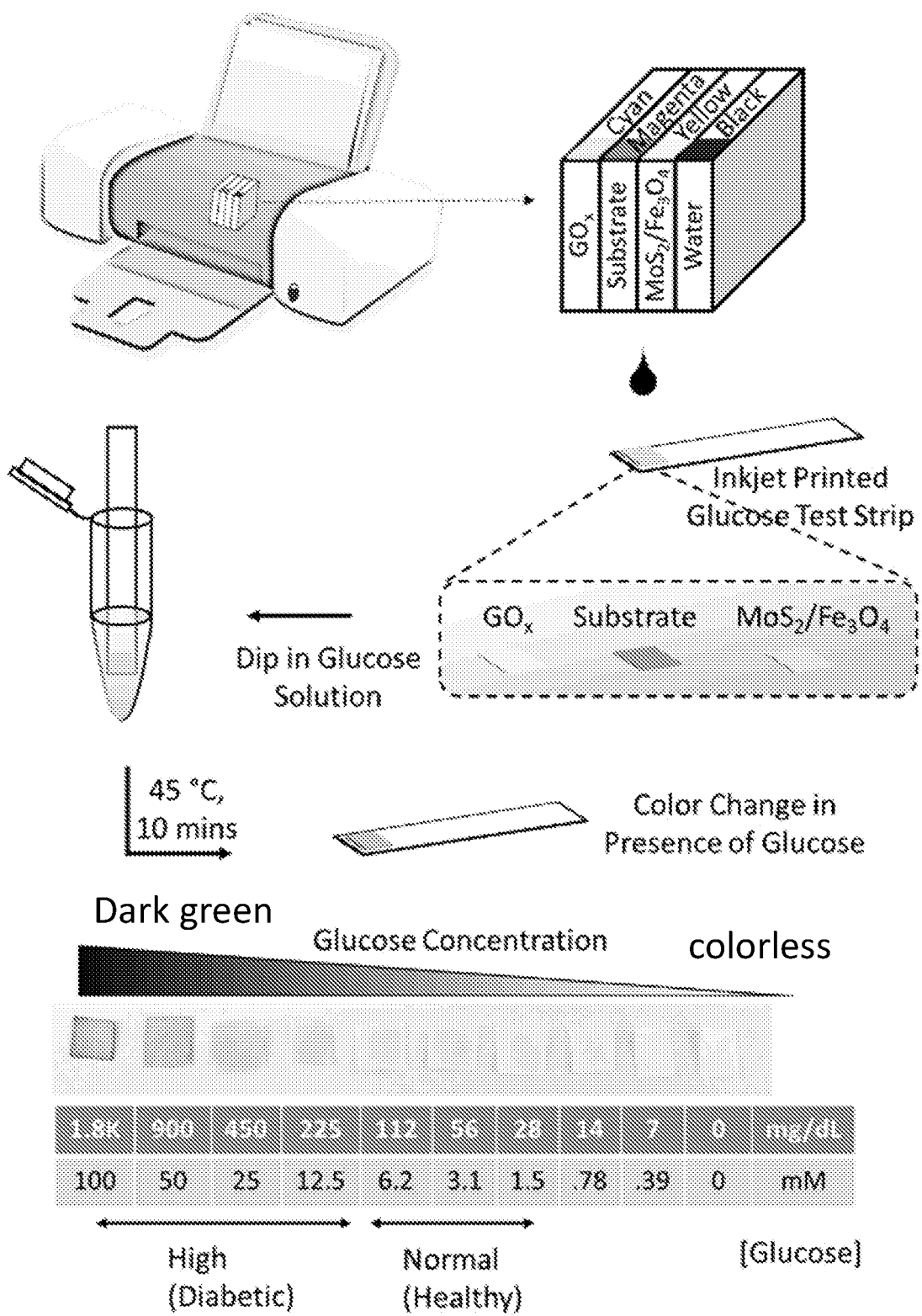
FIG. 9 depicts the development of glucose test strips by inkjet printing solutions of GOx (20 mg/ml), ABTS (1 mM) and $MoS_2/Fe_3O_4$ ([Mo]=8 µg/mL, [Fe]=22 µg/mL). The strip turns from colorless to green and then to dark green in the presence of different concentrations of glucose.
Figure 11:
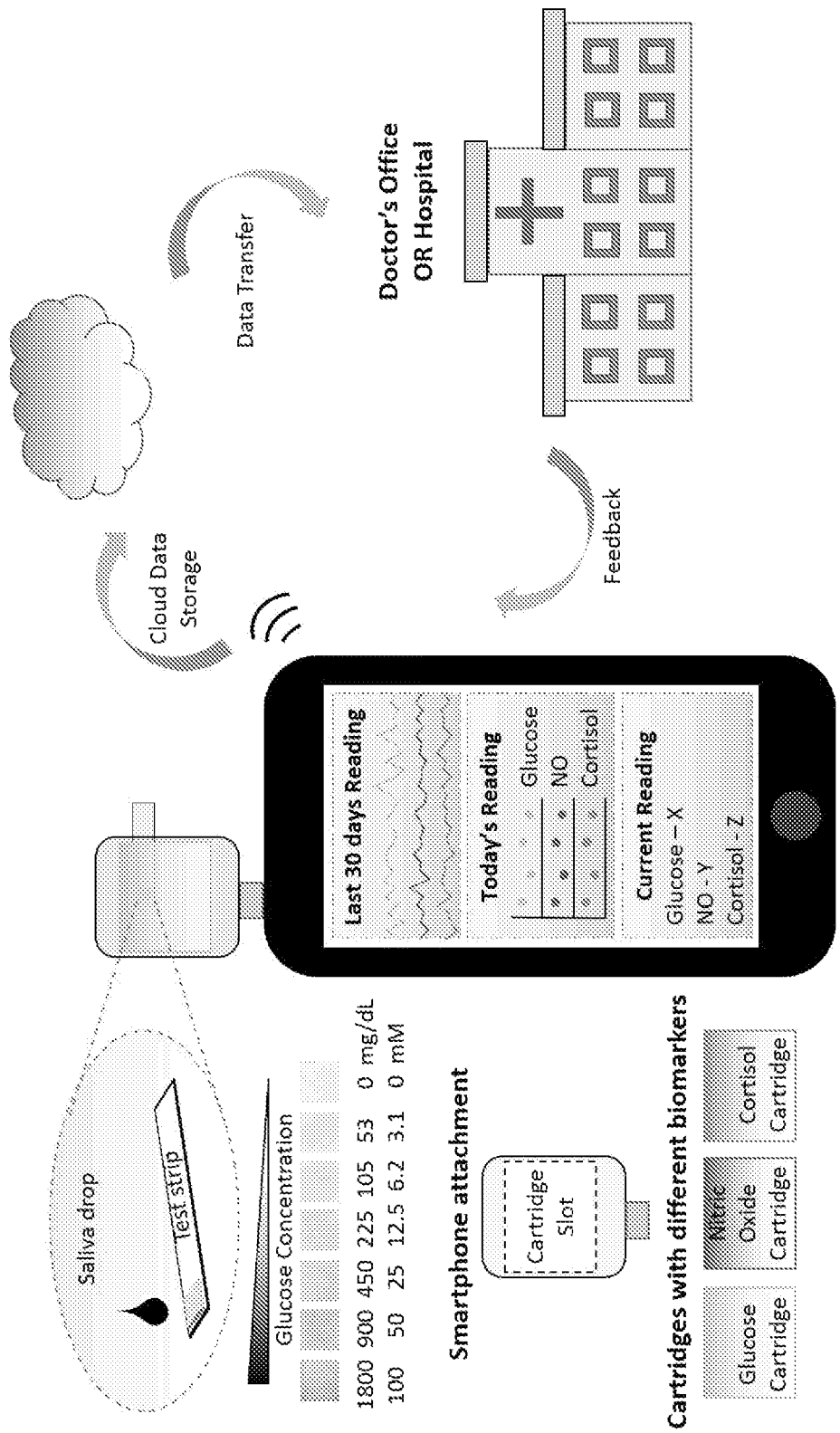
FIG. 11 depicts implementation of the test strip diagnostic platform of FIG. 9 using a smartphone.

As shown in FIG. 11, the test strip diagnostic platform of FIG. 9 can be implemented using a smartphone-based attachment/module for more automated recognition that can monitor the glucose readings. The strip can be inserted into a cartridge-based device where the colorimetric in presence of glucose can be digitally detected. Then, the device can be attached to a smartphone and the data can be collected, sent to physician/clinic and/or stored in the cloud. This can allow the instant feedback from the physician/clinic. The same device can be extended to detect other biomarkers (target analytes) such as nitric oxide and cortisol. For each biomarker, the device can use a different cartridge which has the sensing elements for that biomarker. For example, for nitric oxide and cortisol, the cartridge can be an electrochemical cell. The presence of nitric oxide and cortisol can be detected based on change in current values.

EXAMPLE

Introduction

A novel, one-step method where 2D materials can be exfoliated and stabilized in water using functionalized nanoparticles (NPs), resulting in 2D/0D nanocomposites, is reported here. Liquid exfoliation of 2D materials via organic solvents and ion intercalation has been previously reported.[10-12] Ion intercalation is an environmentally sensitive and time consuming process, and in some cases results in the structural deformation of 2D materials.[13] Exfoliation of 2D materials in organic solvents is promising.[10,14] However, for large scale production, environmentally friendly solvents such as water are preferred.[15] Most of the 2D materials cannot be exfoliated in water without any surfactants or stabilizers.[15] This method uses aqueous dispersion of nanoparticles to exfoliate 2D materials, and is a facile and scalable. Three different 2D materials ($MoS_2$, $WS_2$, BN) have been exfoliated using different NPs ($Fe_3O_4$, Au, QDs) to show the versatile nature of this method. Hence, a library of 2D/0D nanocomposites was developed.

To demonstrate the application of 2D/0D nanocomposites, $MoS_2$/$Fe_3O_4$ nanocomposites were prepared and their peroxidase-like catalytic property was studied. $MoS_2$/$Fe_3O_4$ nanocomposite demonstrated significantly higher peroxidase activity than both $MoS_2$ nanosheets and $Fe_3O_4$ nanoparticles. The enhanced peroxidase activity resulted in lower limit of detection for $H_2O_2$ and glucose.[16-17] Finally, a paper based sensor has been developed by inkjet printing $MoS_2$/$Fe_3O_4$ test strips and showing their application towards point-of-care diagnostics.

Experimental

Materials $MoS_2$ powder, SDS, GOx, TMB, OPD, ABTS, fructose, lactose and maltose were purchased from Sigma Aldrich.

Preparation of $MoS_2$/$Fe_3O_4$ nanocomposites 50 mg of $MoS_2$ powder, 0.2 ml of thiol functionalized $Fe_3O_4$ nanoparticles ([Fe]=1 mg/ml) and 10 mL of milli-q water were probe sonicated for 10 mins. The solution was then centrifuged at 4500 rpm for 15 mins, and the green-brown supernatant was collected and dialyzed using a dialysis bag (MWCO=10 000) for 6 hours in water. Any aggregated particles were removed by centrifugation. Finally, dispersion of $MoS_2$/$Fe_3O_4$ nanocomposite was stored at room temperature and used as is for further experiments. The concentration of Mo and Fe was calculated via ICP. The preparation is illustrated in Scheme 1, FIG. 10.

Preparation of $MoS_2$ Nanosheets 50 mg of $MoS_2$ powder, 15 mg of SDS and 10 mL of milli-q water were probe sonicated for 10 mins. The solution was then centrifuged at 4500 rpm for 15 mins, and the green supernatant was collected and dialyzed (MWCO=10 000) for 6 hours. Any aggregated particles were removed by centrifugation. Finally, dispersion of $MoS_2$ nanosheets was stored at room temperature and used as is for further experiments.

Synthesis of $Fe_3O_4$ Nanoparticles

The $Fe_3O_4$ nanoparticles were synthesized using a previously reported thermal decomposition method that resulted in monodispersity and single crystallinity.[18-19] In a typical $Fe_3O_4$ nanoparticles synthesis, Fe(acac)3 (2 mmol), 1,2-hexadecanediol (10 mmol), oleic acid (6 mmol), oleylamine (6 mmol), and benzyl ether (20 mL) were charged in a 100 mL three-neck round-bottom flask and magnetically stirred under a flow of nitrogen. The mixture was first heated to 110° C. for 1 h to remove moisture. The temperature was then increased to 210° C. for 1 h, and was finally refluxed for 1 h before cooling down to room temperature. The black-brown mixture was precipitated, washed three times using ethanol, and dispersed in hexane.

Preparation of Thiol Functionalized $Fe_3O_4$ Nanoparticles

The as-synthesized oleic acid coated hydrophobic $Fe_3O_4$ nanoparticles were functionalized with MUA and citric acid (CA) via ligand exchange process.[18] Chloroform dispersion (2 ml) of $Fe_3O_4$ nanoparticles (12.5 mg) and DMSO solution of MUA (1 ml, 62.5 mg) and CA (1 ml) of were mixed and sonicated overnight at room temperature under $N_2$ protection. The modified $Fe_3O_4$ nanoparticles were washed by dichloromethane 3 times, dried under nitrogen gas, and dispersed in water. The dispersion was dialyzed to remove any residual surfactants using a dialysis bag (MWCO=10 000) for 2 days in water. A 200 nm syringe filter was used to remove any precipitation, and the final concentration of thiol functionalized $Fe_3O_4$ nanoparticles dispersed in water was determined by ICP-MS analysis. TEM showed that the particles did not aggregate after ligand exchange, and hydrodynamic sizes were found in the range of 22-47 nm.

4.3 Peroxidase Activity of $MoS_2/Fe_3O_4$

Peroxidase-like activity of $MoS_2/Fe_3O_4$ nanocomposite was tested by mixing 0.2 ml of TMB (1 mM), 0.2 ml of $MoS_2/Fe_3O_4$ ([Mo]=8 µg/mL, [Fe]=22 µg/mL) and 0.2 mL $H_2O_2$ (100 mM). TMB (3,3',5,5'-tetramethylbenzidine) solution was made in 0.1 M citrate-phosphate buffer (pH 5.0). For ABTS (2,2'-Azinobis [3-ethylbenzothiazoline-6-sulfonic acid]-diammonium salt) and OPD (o-phenylenediamine dihydrochloride) reaction, a similar method was used. OPD was dissolved in 0.1 M citrate-phosphate buffer (pH 5.0) while ABTS was dissolved in 0.1 M citrate buffer (pH 5.0).

Characterization of $Fe_3O_4$, $MoS_2$, and $MoS_2/Fe_3O_4$

Transmission electron microscopy (TEM), energy dispersive X-ray (EDX), and elemental mapping of the nanostructures were observed using a Hitachi HD2300. The hydrodynamic diameters of the nanostructures were measured by a Malvern Zeta Sizer Nano S-90 dynamic light scattering (DLS) instrument. Raman spectra were collected on the HORIBA LabRAM HR Evolution Confocal Raman System equipped with a solid-state laser. The laser power used was 8.8 uW with a co-condition of 2. X-ray photoelectron spectroscopy (XPS, Thermo Scientific ESCALAB 250Xi) was used for binding energy analysis.

Detection of $H_2O_2$ and Glucose in Solution

For $H_2O_2$ detection, first 0.2 ml of TMB (1 mM) in pH 5.0 citrate phosphate buffer and 0.2 ml of $MoS_2/Fe_3O_4$ ([Mo]=8 µg/mL, [Fe]=22 µg/mL) were mixed. Then, different concentrations of 0.2 mL $H_2O_2$ were added. A reaction rate of 652 nm was recorded immediately after the addition of $H_2O_2$, while for the absorbance values, the solutions were kept at room temperature for 5 mins before recording. The absorbance change was recorded in BioTek Synergy 4 Multimode plate reader with onboard dispenser and monochromator.

For glucose detection, a mixture of 0.1 mL GOx (20 mg/mL) and 0.1 mL of glucose solution of different concentrations in 0.1 M Na2HPO4 buffer (pH 7.0) was incubated at 37° C. for 30 min. Then, 0.2 ml of TMB (1 mM) in pH 5.0 citrate phosphate buffer and 0.2 mL of $MoS_2/Fe_3O_4$ ([Mo]=8 µg/mL, [Fe]=22 µg/mL) were added. The solutions were kept at 45° C. for 10 mins, and then the absorbance change was recorded in the plate reader. For fructose, lactose and maltose, a similar method was used, except glucose was replaced with one of fructose, lactose or maltose.

Preparation of Test Strips

A desktop inkjet color printer Epson Workforce 30 was used to print glucose test strips. The standard cyan, magenta and yellow ink cartridges were replaced with cartridges filled with GOx, chromogenic substrate (ABTS) and $MoS_2/Fe_3O_4$ solutions. The main reason for this choice of printer was its piezoelectric print heads that use pressure rather than heat, since heat can potentially denature GOx. Test strips were developed by printing layers of each solution in the form of a square on the paper and drying at room temperature. Finally the strips were stored in 4° C. until further usage.

Detection of Glucose Via Test Strips

Test strips were dipped into glucose solution of different concentrations for 1 min. After that, they were kept in an oven set at 45° C. for 10 minutes, and the color change was observed with naked eye.

Results and Discussion

Figure 1B:
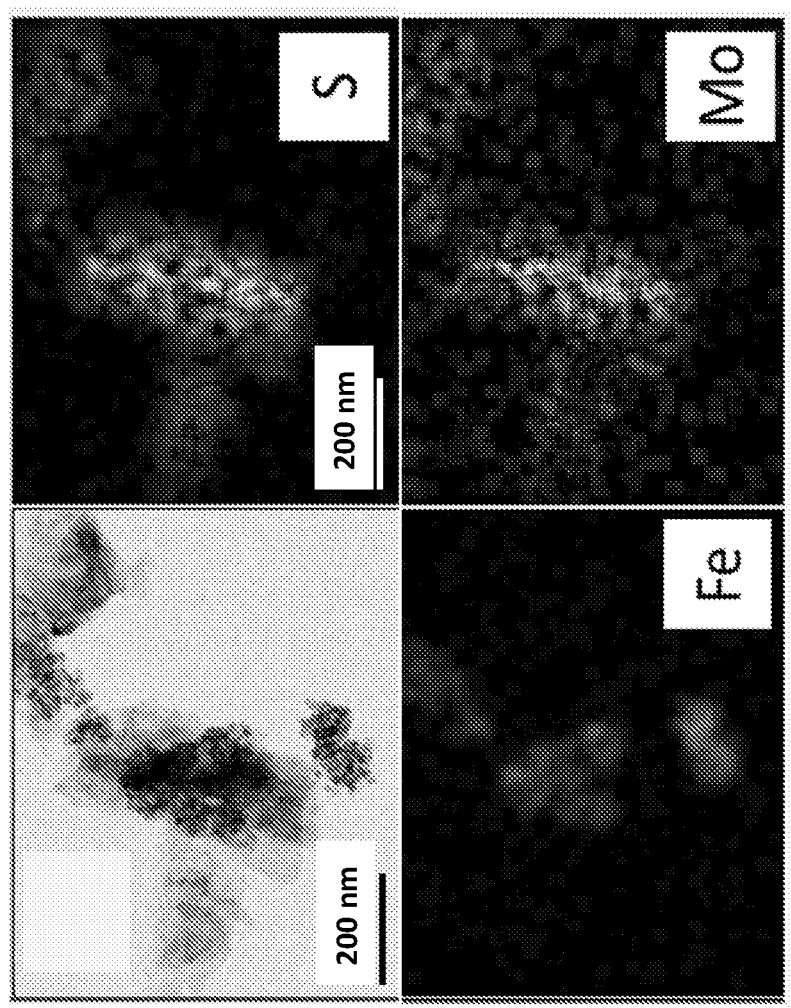
FIG. 1B depicts elemental mapping of the nanocomposite.
Figure 1C:
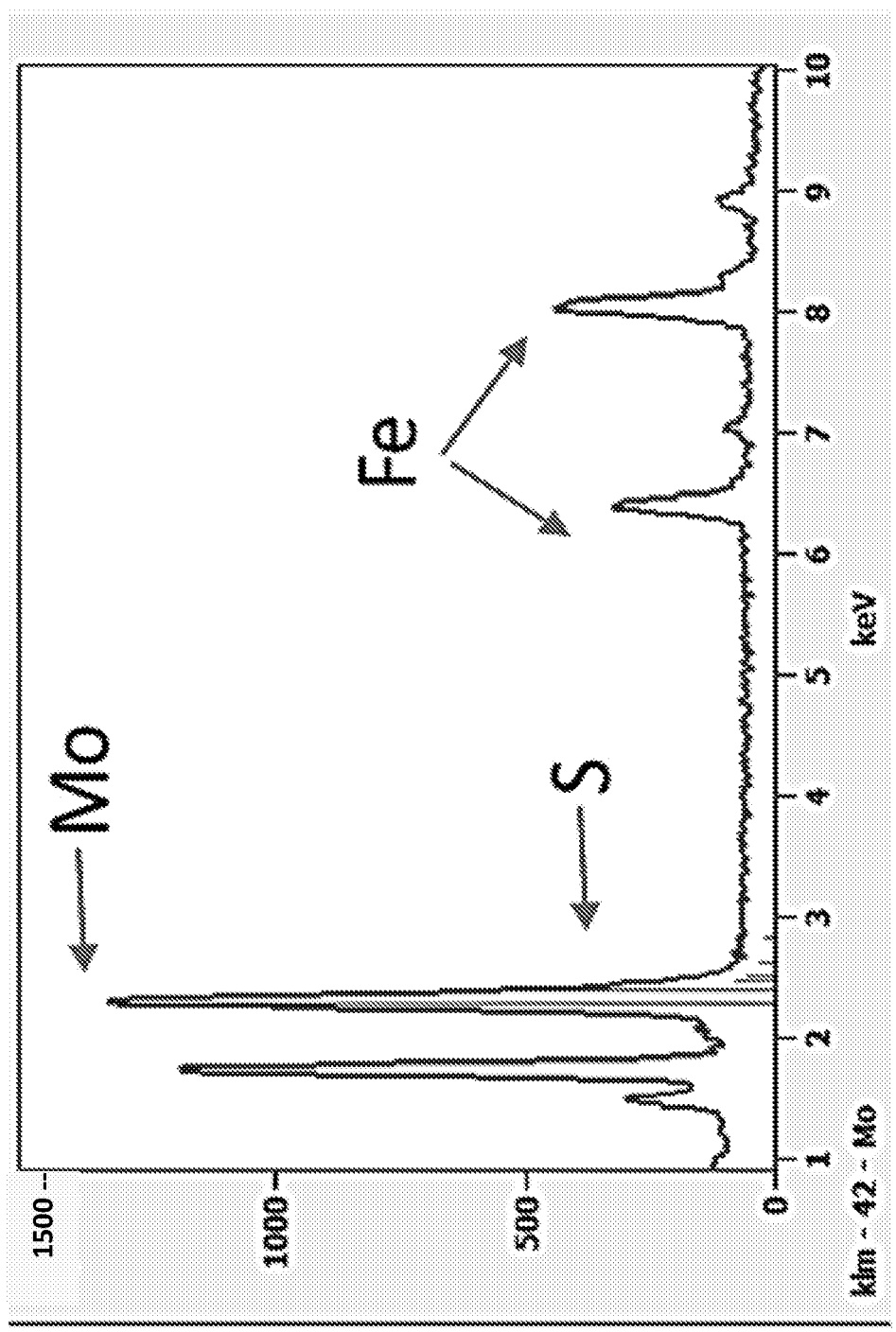
FIG. 1C depicts the EDX of the nanocomposite.

TEM images of $MoS_2/Fe_3O_4$ nanocomposites showed that $Fe_3O_4$ NPs were decorated on the surface of $MoS_2$ nanosheets (FIG. 1A). The size of the $Fe_3O_4$ nanoparticles used was about 8 nm. The $Fe_3O_4$ NPs acted as stabilizers for $MoS_2$ sheets and helped them disperse in water. FIGS. 1B and 1C show an elemental map and EDX patterns, respectively, of $MoS_2/Fe_3O_4$. The Fe, Mo, and S signals from the same area confirm the presence of $Fe_3O_4$ nanoparticles on exfoliated $MoS_2$ nanosheets.

Figure 2A:
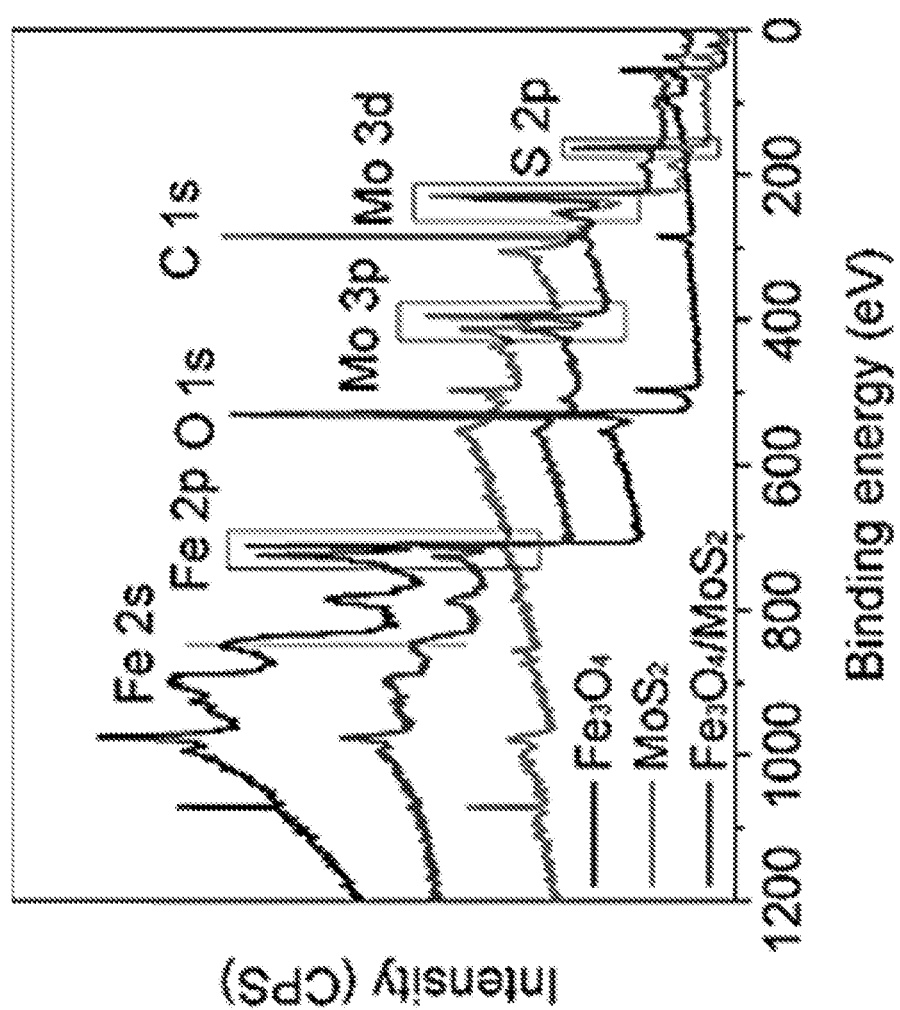
FIG. 2A shows an XPS full line scan of $Fe_3O_4$ nanoparticles, $MoS_2$ nanosheets, and $MoS_2/Fe_3O_4$ nanocomposite.

The integration of $MoS_2$ nanosheets and $Fe_3O_4$ NPs was also confirmed by X-ray photoelectron spectroscopy (XPS) and Raman spectroscopy. XPS was used to determine the chemical composition and chemical states of the $MoS_2/Fe_3O_4$ nanocomposite. As shown in full line scans in FIG. 2A, the XPS spectrum of $MoS_2/Fe_3O_4$ nanocomposite showed characteristic peaks of both $MoS_2$ (100-400 eV) and $Fe_3O_4$ (700-900 eV) NPs, confirming the existence of both $MoS_2$ and $Fe_3O_4$ in the nanocomposite.

Figure 2B:
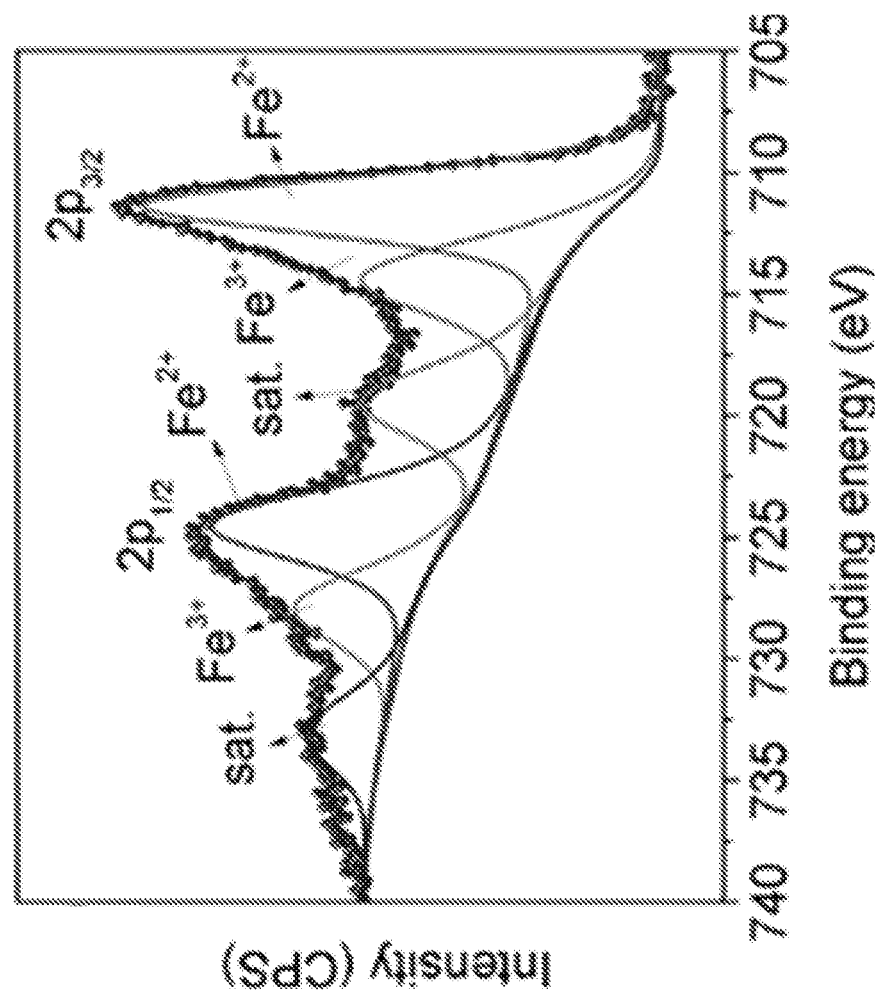
FIG. 2B depicts a detailed scan of $MoS_2/Fe_3O_4$ nanocomposite with characteristic peaks of Fe.
Figure 2C:
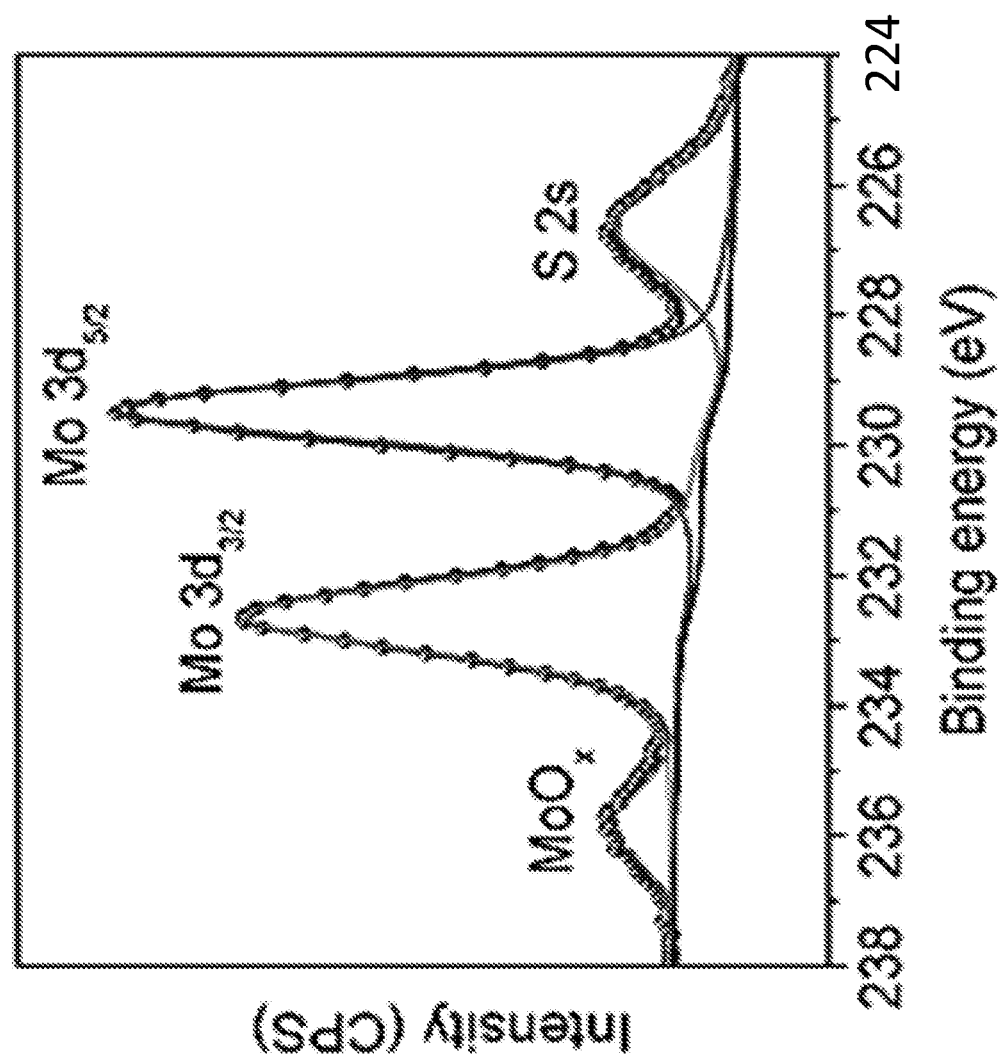
FIG. 2C depicts a detailed scan of $MoS_2/Fe_3O_4$ nanocomposite with characteristic peaks of Mo.
Figure 2D:
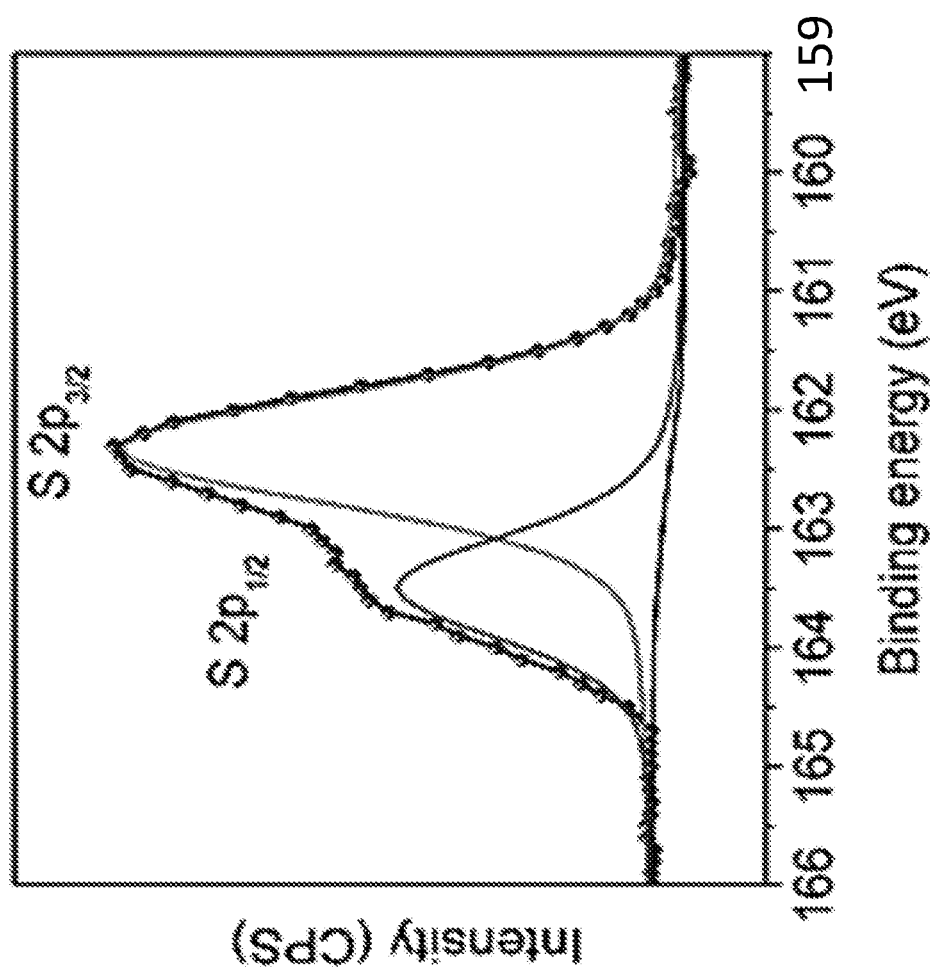
FIG. 2D shows a detailed scan of $MoS_2/Fe_3O_4$ nanocomposite with characteristic peaks of S.

FIGS. 2B-2D show the detailed scan of the $MoS_2/Fe_3O_4$ nanocomposite with characteristic peaks of Fe, Mo, and S. The Fe spectrum in the $2p_{3/2}$ region can be deconvoluted into two main peaks and a satellite peak (FIG. 2B). The same pattern was repeated, with almost half intensity for the $2p_{1/2}$ component. $Fe_3O_4$ comprises two oxidation states, $Fe^{2+}$ and $Fe^{3+}$. The lowest binding energy peak at 710.2 eV was attributed to Fe', with a corresponding satellite at 718.0 eV. The Fe' peak was found with a binding energy of 713.3 eV. The peaks position of Fe $2p_{3/2}$ and $Fe_2p_{1/2}$ are comparable to the reported values in the literature.[20-22]

FIG. 2C displays Mo 3d peaks at 233.04 eV and 229.87 eV, corresponding to the $3d_{5/2}$ and $3d_{3/2}$ doublet. The S 2p peak can be deconvoluted into two peaks at 163.88 eV and 162.70 eV (FIG. 2D), attributing to the $2p_{1/2}$ and $2p_{3/2}$ orbital. These binding energy values are consistent with those reported in previous studies and confirm the expected charge states of $Mo^{4+}$ and $S^{2-}$ in the $MoS_2$ nanosheets.[23-24] It is also worth noting that additional peaks of metallic Mo or $MoO_x$ were not observed in higher/lower binding energy regions, which confirms the quality of exfoliated $MoS_2$ nanosheets similar as CVD grown $MoS_2$.

Figure 3A:
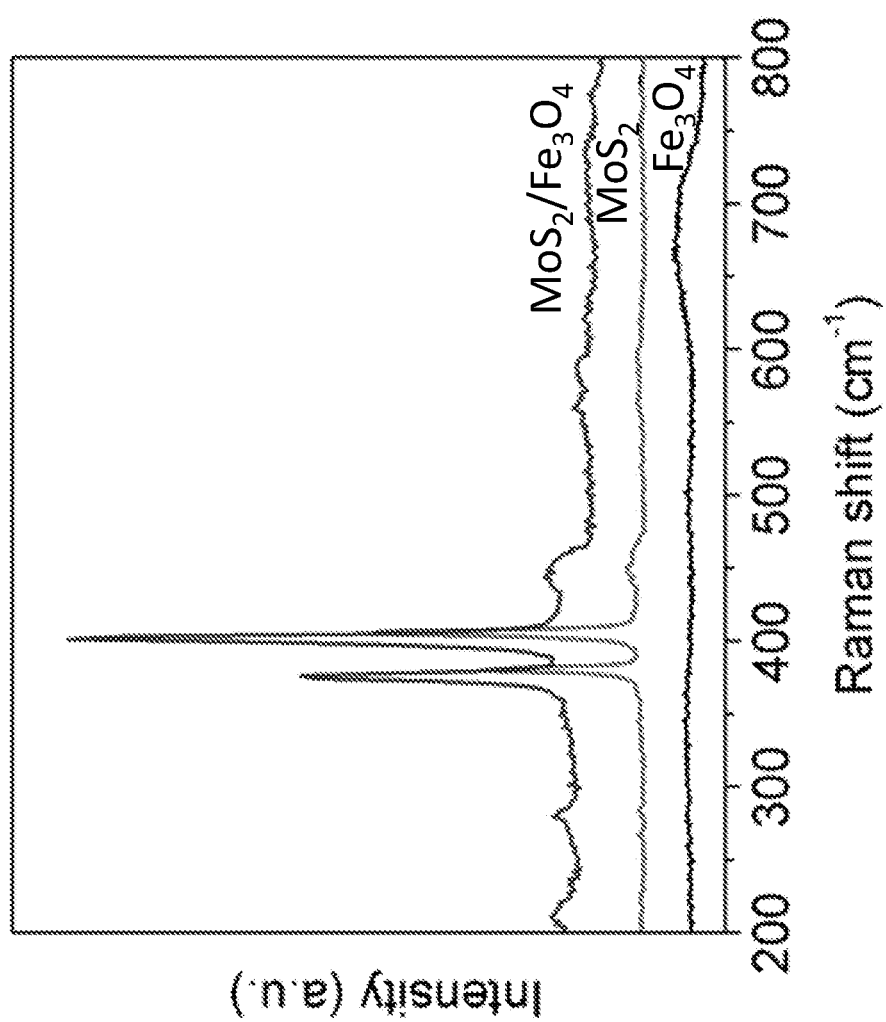
FIGS. 3A and 3B depict Raman spectroscopy of $Fe_3O_4$ nanoparticles, $MoS_2$ nanosheets, and $MoS_2/Fe_3O_4$ nanocomposite.
Figure 3B:
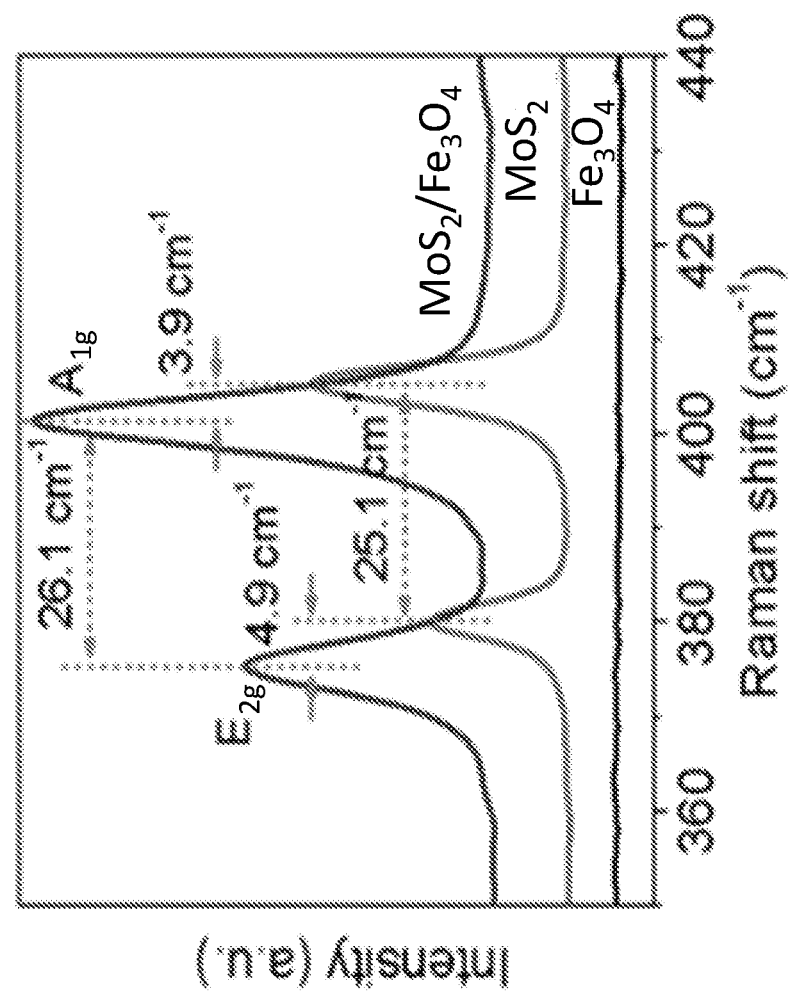

Raman spectroscopy can assess the crystallinity and layer thickness of two-dimensional $MoS_2$ in terms of the position and frequency difference of two characteristic vibrational modes, $E_{2g}$ and $A_{1g}$.[24-25] The $E_{2g}$ mode is attributed to the in-plane vibration of Mo and S atoms, while the $A_{1g}$ mode is related to the out-of-plane vibration of S atoms.[25] FIG. 3A shows the Raman spectra of $MoS_2/Fe_3O_4$ nanocomposites, $MoS_2$ nanosheets and $Fe_3O_4$ NPs dispersed on a Si/$SiO_2$ substrate. The measurements were conducted using a solid-state laser (532 nm) with power of 8.8 μW to eliminate the effect of optical heating. FIG. 3B shows the two vibrational modes centered at 380.7 $cm^{-1}$ and 405.6 $cm^{-1}$, while the multilayer $MoS_2$ sheet exhibits modes at 383.8 $cm^{-1}$ and 408.6 $cm^{-1}$. Both spectra gave similar $E_{2g}$-to-$A_{1g}$ frequency differences of ~25 $cm^{-1}$. This value was smaller than that of bulk $MoS_2$, but higher than single layer $MoS_2$, indicating their exfoliated few layer structure.[26] Raman spectroscopy has also been utilized to investigate the effects of lattice strain, doping levels, and the van der Waals interaction at the interface of 2D crystals.[25] The in-plane Raman mode, $E_{2g}$, is sensitive to the built-in strain of 2D $MoS_2$, while the out-of-plane mode, $A_{1g}$, is a reflection of interlayer van der Waals interactions. Thus, it is reasonable to predict from the $A_{1g}$ shift of 3.9 $cm^{-1}$ from $MoS_2$ to $MoS_2/Fe_3O_4$ that integration of $Fe_3O_4$ nanoparticles caused in-plane strain in $MoS_2$ nanosheets.

Figure 4A:
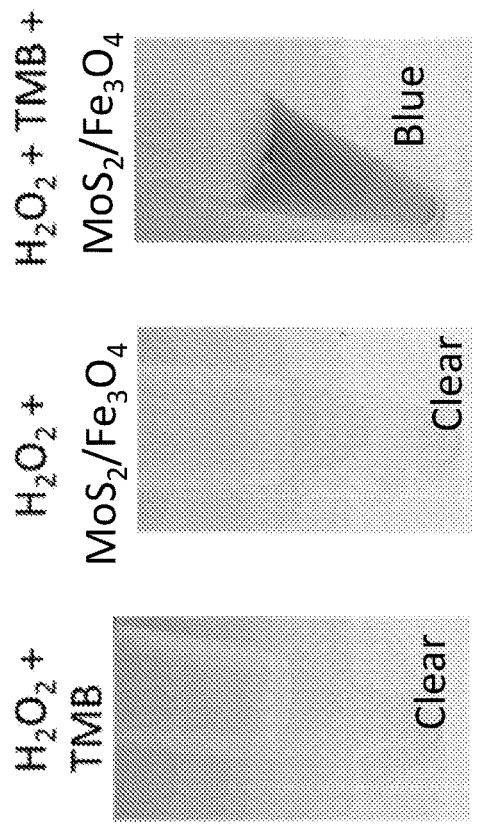
FIG. 4A depicts a demonstration of peroxidase-like activity of $MoS_2/Fe_3O_4$ nanocomposite in pH 5.0 citrate phosphate buffer at room temperature. Color change was only observed in solution of $H_2O_2$+TMB+$MoS_2/Fe_3O_4$ while solutions of $H_2O_2$+TMB and $H_2O_2$+$MoS_2/Fe_3O_4$ remained colorless. [TMB] was 1 mM, and [Mo] and [Fe] were 8 and 22 µg/mL in $MoS_2/Fe_3O_4$.
Figure 4B:
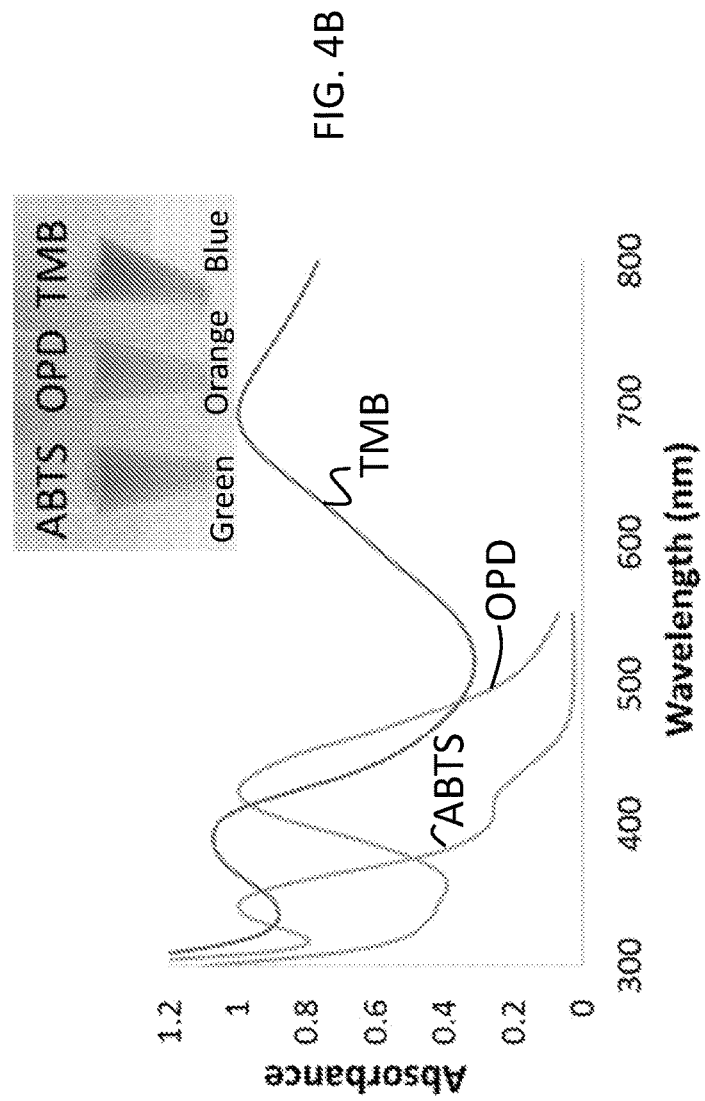
FIG. 4B shows that, similar to TMB, the other chromogenic substrates such as ABTS and OPD were also oxidized and resulted in green and orange colors, respectively. Absorbance plots and a picture (inset) of oxidized substrates (ABTS, OPD, and TMB) in the presence of $H_2O_2$ are shown.

The peroxidase-like catalytic activity of $MoS_2/Fe_3O_4$ nanocomposites was tested in solution of chromogenic substrate 3,3',5,5'-tetramethylbenzidine (TMB) and $H_2O_2$.[17, 27] As shown in FIG. 4A, a solution of $H_2O_2$+TMB+$MoS_2/Fe_3O_4$ turned blue within seconds, while a solution of $H_2O_2$+TMB showed negligible color change, confirming the $Fe_3O_4$ accelerated the color change. As a negative control, a solution of $H_2O_2$+$MoS_2/Fe_3O_4$ was also prepared that remained colorless due to the absence of TMB. (FIG. 4B). TMB is oxidized in the presence of $H_2O_2$, and the reaction was catalyzed by the $MoS_2/Fe_3O_4$ nanocomposites, resulting in quick formation a blue complex.[27] Similar to TMB, the other chromogenic substrates such as 2,2'-Azinobis [3-ethylbenzothiazoline-6-sulfonic acid]-diammonium salt (ABTS) and o-phenylenediamine dihydrochloride (OPD) were also mixed with $MoS_2/Fe_3O_4$ and $H_2O_2$ and resulted in green and orange colors, respectively.[28] FIG. 4B shows absorbance plots and a picture (inset) of colored (oxidized) substrates (ABTS, OPD, and TMB) in the presence of $H_2O_2$. These results demonstrate that $MoS_2/Fe_3O_4$ nanocomposite demonstrates peroxidase-mimic properties and can be used as an inorganic and robust catalyst for various peroxidase reactions.

Figure 5A:
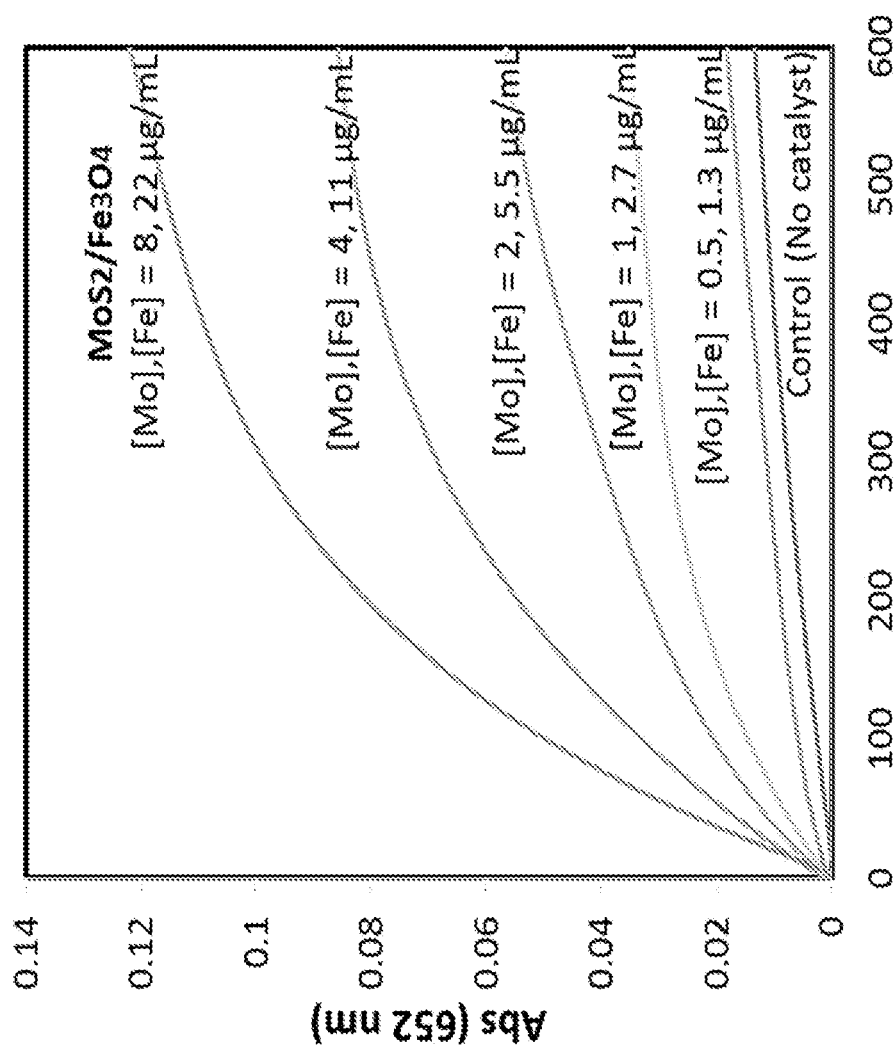
FIG. 5A shows the time-dependent absorbance changes at 652 nm in the presence of 100 mM $H_2O_2$ and 1 mM TMB at different concentrations of $MoS_2/Fe_3O_4$.
Figure 5B:
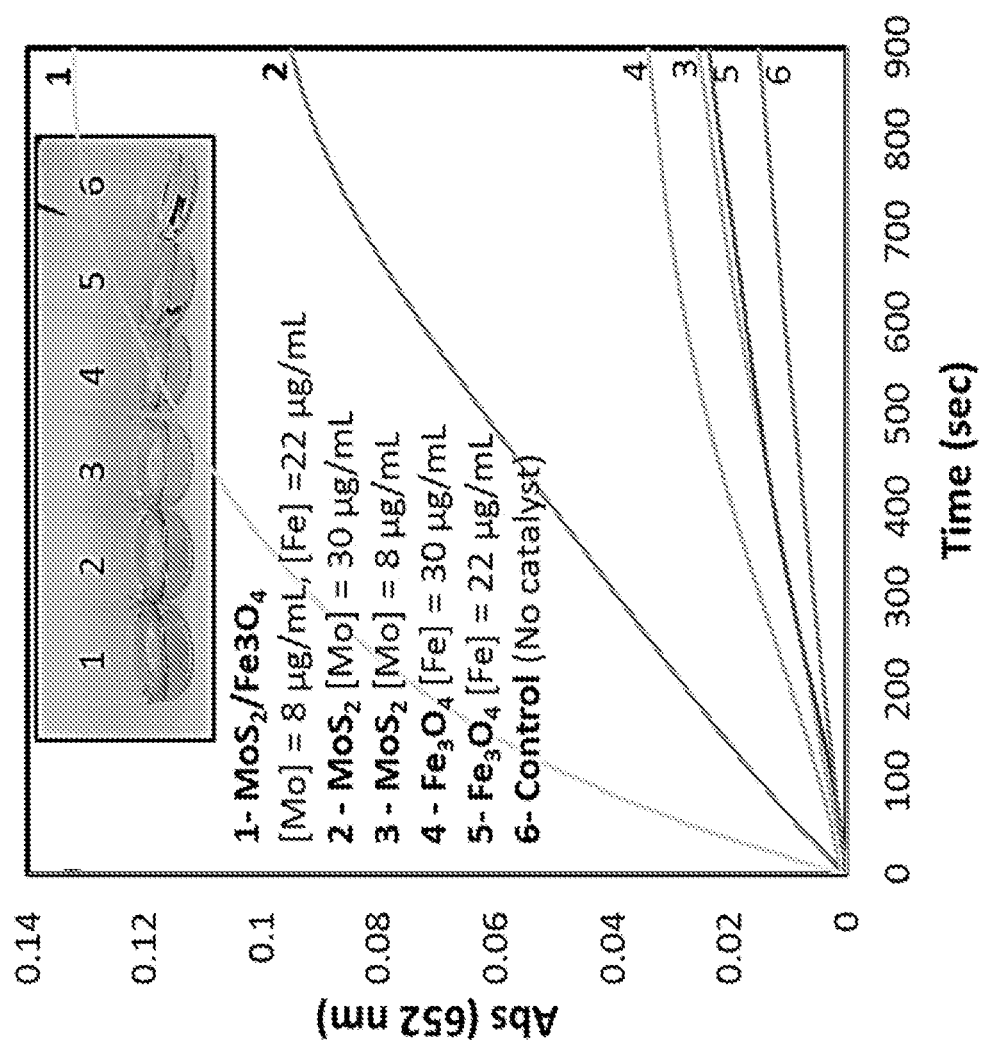
FIG. 5B shows the time-dependent absorbance changes at 652 nm in presence of 100 mM $H_2O_2$ and 1 mM TMB at different concentrations of $MoS_2/Fe_3O_4$, $MoS_2$, and in the presence of $Fe_3O_4$ at room temperature.

The catalytic reaction was monitored by noting the change in absorbance of converted TMB at 652 nm.[27] FIG. 5A shows the time-dependent absorbance changes when different concentrations of $MoS_2/Fe_3O_4$ nanocomposite were added to $H_2O_2$ and TMB solutions. The incremental change in the reaction rate with increasing $MoS_2/Fe_3O_4$ concentration shows that the catalytic behavior follows typical Michaelis-Menten kinetics.[29] To compare with $MoS_2/Fe_3O_4$ nanocomposite, peroxidase activity of $Fe_3O_4$ nanoparticles and $MoS_2$ nanosheets was analyzed (FIG. 5B). The kinetic analysis showed that the reaction rate of $MoS_2/Fe_3O_4$ nanocomposite was significantly higher than $MoS_2$ nanosheets and $Fe_3O_4$ nanoparticles with similar Mo and Fe concentrations, respectively.[27] Though $Fe_3O_4$ nanoparticles and $MoS_2$ nanosheets alone were peroxidase active, the $MoS_2/Fe_3O_4$ nanocomposites showed superior catalytic activity over their individual components. The integration of $Fe_3O_4$ NPs on large area 2D $MoS_2$ nanosheets increased the catalytic sites.

These synergistic effects in the $MoS_2/Fe_3O_4$ nanocomposite contributed to the superior peroxidase activity.[30]

Figure 6A:
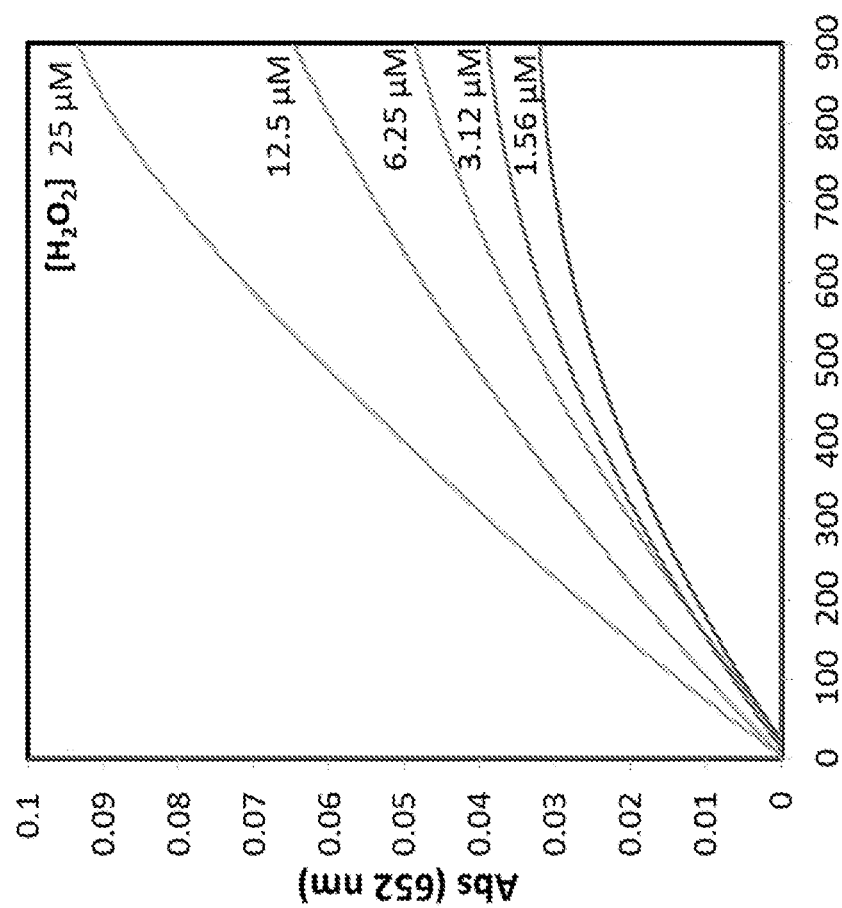
FIGS. 6A and 6B depict time-dependent absorbance changes at 652 nm in presence of at different concentrations of $H_2O_2$ in pH 5.0 citrate phosphate buffer at room temperature. [TMB] was 1 mM, and [Mo] and [Fe] were 8 and 22 µg/mL in $MoS_2/Fe_3O_4$.
Figure 6B:
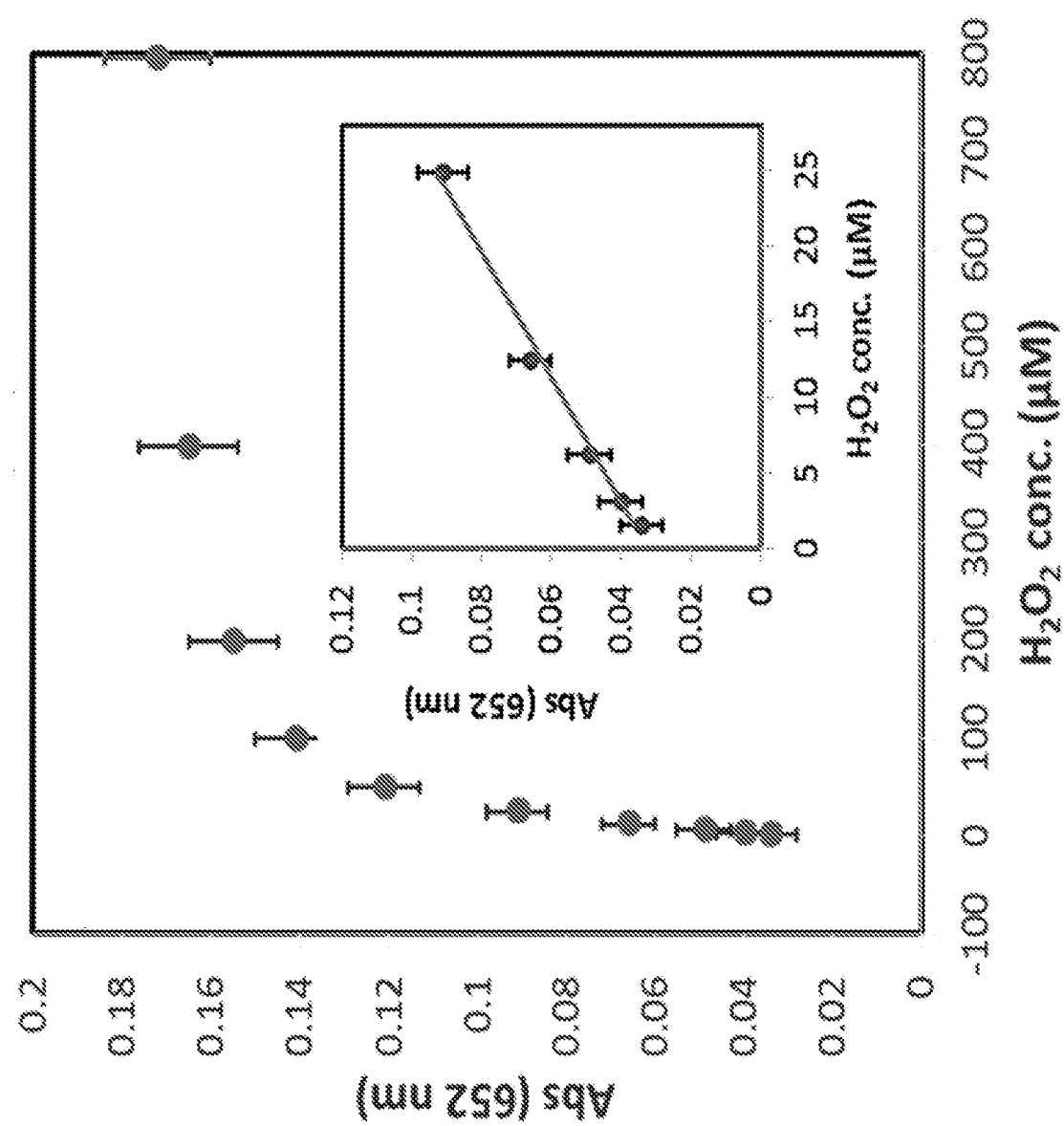

Based on the intrinsic peroxidase-like activity, a colorimetric detection method for $H_2O_2$ was designed.[16] Oxidation of TMB was observed at different $H_2O_2$ concentrations in the presence of $MoS_2/Fe_3O_4$ and TMB. The concentration of $MoS_2/Fe_3O_4$ was kept constant and the change in absorbance values was observed at 652 nm (FIG. 6A). The changed in absorbance was detected down to 1.56 μM of $H_2O_2$. The kinetic analysis suggested that the reaction rate was also dependent on $H_2O_2$ concentration (FIG. 6B).

Figure 7B:
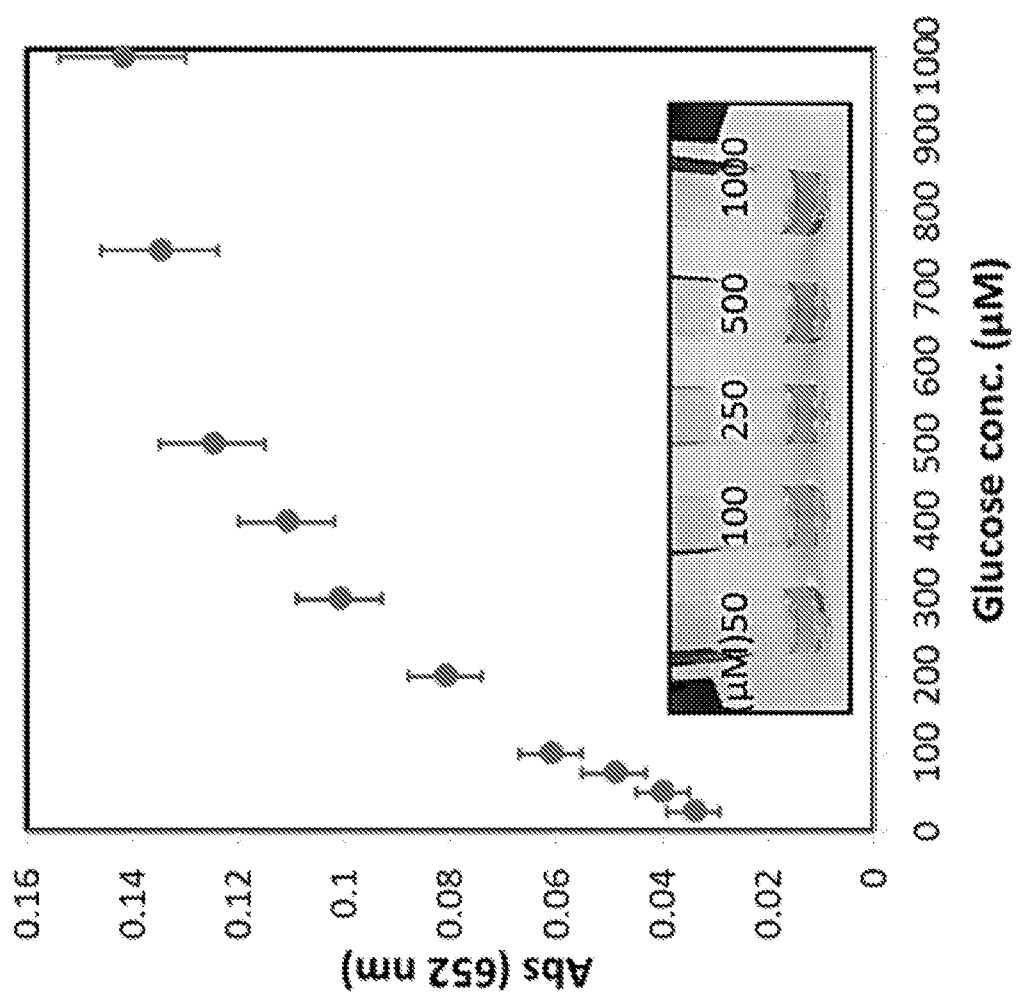
FIG. 7B depicts dose dependent behavior for glucose detection in the presence of GOx, TMB, and $MoS_2/Fe_3O_4$, as well as absorbance values at different concentrations of glucose in the presence of GOx (20 mg/ml), TMB (1 mM) and $MoS_2/Fe_3O_4$ ([Mo]=8 µg/mL, [Fe]=22 µg/mL).

$H_2O_2$ is the key component in the conventional electrochemical glucose sensors that are based on oxidation reaction of glucose catalyzed by glucose oxidase.[31-32] Since $H_2O_2$ can be colorimetrically detected using $MoS_2/Fe_3O_4$, a colorimetric method was designed to detect glucose. When glucose solution was added in a mixture of GOx, TMB, and $MoS_2/Fe_3O_4$, the solution turned blue (or orange with OPD, or green with ABTS). The reaction is shown in the FIG. 7A. The freshly produced $H_2O_2$ from glucose-GOx reaction oxidized TMB that resulted in a blue color. FIG. 7B shows absorbance value obtained when solutions of different glucose concentration were mixed with GOx, TMB, and $MoS_2/Fe_3O_4$. The change in absorbance was detected down to 25 μM of glucose.

Figure 8A:
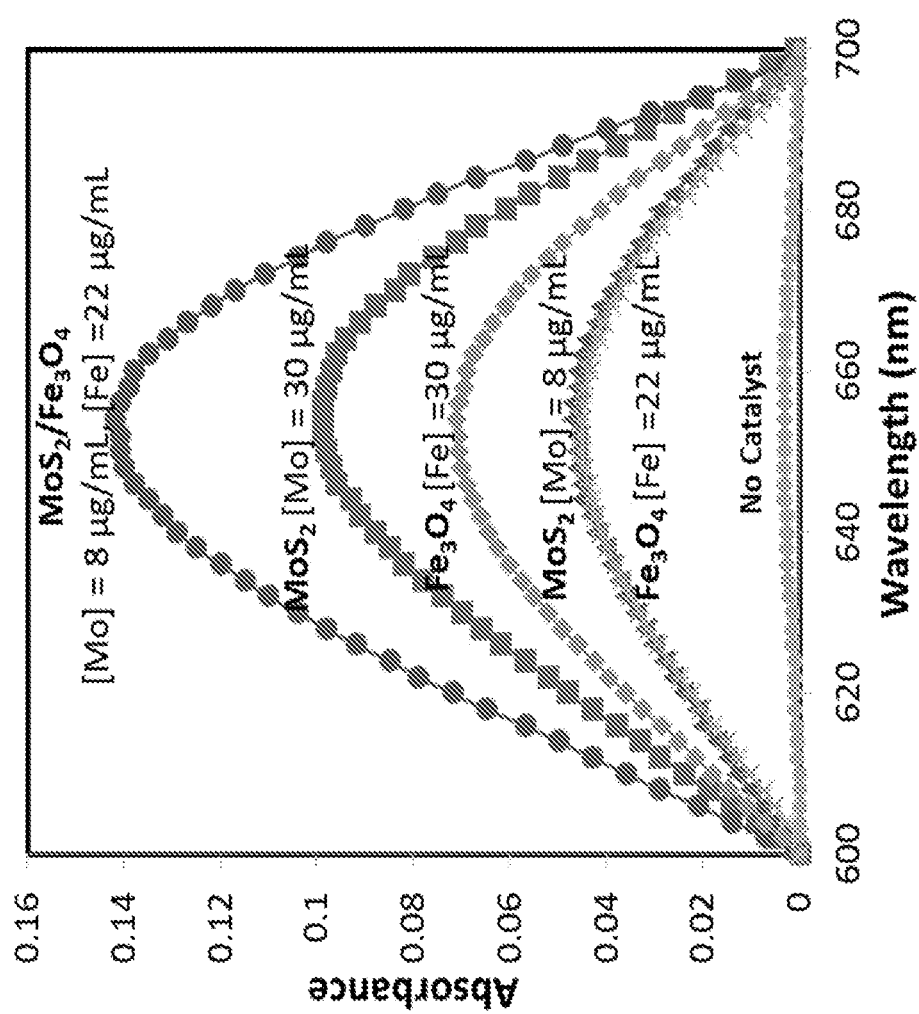
FIG. 8A depicts absorbance plots in the presence of 1 mM glucose solution with different concentrations of $MoS_2/Fe_3O_4$, $MoS_2$ and $Fe_3O_4$ in presence of 50 µL GOx (20 mg/ml), 50 µL TMB (1 mM).
Figure 8B:
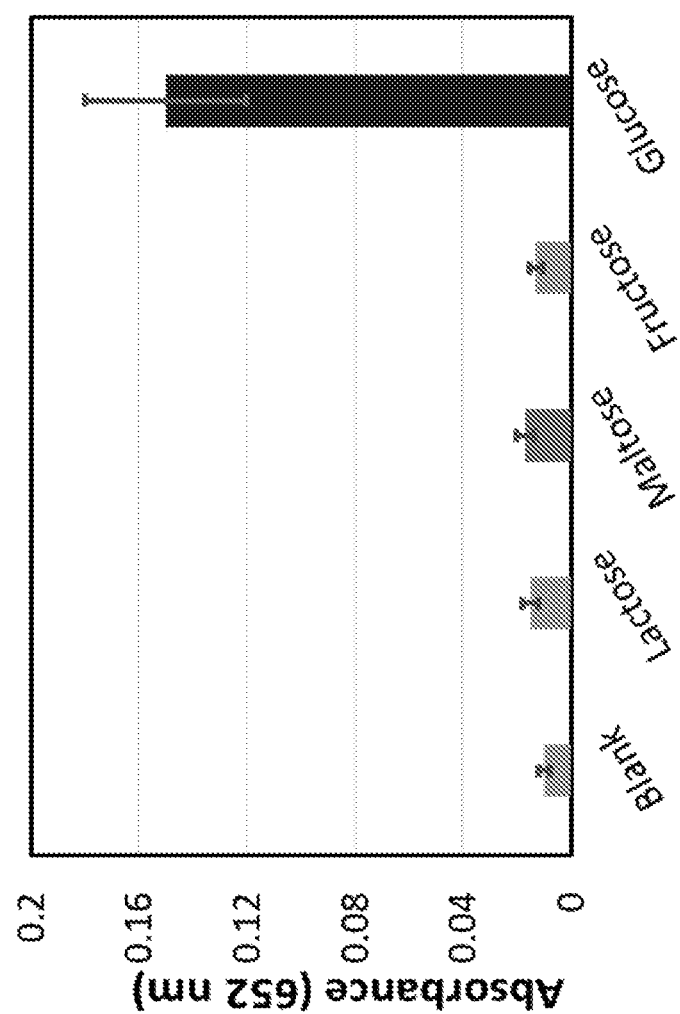
FIG. 8B depicts the selectivity analysis of this detection method by monitoring the absorbance of glucose analogues, as well as fructose, lactose, and maltose in the presence of GOx, TMB, and $MoS_2/Fe_3O_4$. The sharp color change in only the glucose solution demonstrates the highly selective nature of the method.

The glucose detection ability of $MoS_2/Fe_3O_4$ nanocomposite was compared with $Fe_3O_4$ nanoparticles and $MoS_2$ nanosheets with 1 mM glucose solution (FIG. 8A). The highest absorbance values showed that the catalytic efficiency of $MoS_2/Fe_3O_4$ nanocomposite was significantly higher than $MoS_2$ nanosheets and $Fe_3O_4$ nanoparticles with similar Mo and Fe concentrations, respectively. To show the selectivity of this glucose detection method, a set of control experiments was performed in the presence of glucose analogues (FIG. 8B). Solutions of fructose, lactose, and maltose were added in a mixture of GOx, TMB, and $MoS_2/Fe_3O_4$, and their absorbance was observed. The negligible change in absorbance in all of the fructose, maltose, and lactose solutions demonstrates the highly selective nature of this glucose detection method.

Point-of-care glucose diagnostics is still an early concept and has not been widely accepted. Most of the glucose sensing is done by a conventional glucometer where a drop of blood is deposited on a test strip and the glucose concentration is electrochemically detected. Glucose urine test strips are available, but concentration of glucose in urine does not match the accurate blood glucose concentration. Hence, strips that required no blood pricking and can tell accurate blood concentration very quickly can achieve non-invasive POC glucose diagnostics.

This glucose detection method and $MoS_2/Fe_3O_4$ catalyst can accomplish this goal. Based on the colorimetric detection of glucose using $MoS_2/Fe_3O_4$, GOx, and a peroxidase substrate, test strips have been developed that show quick change in color in glucose solution (FIG. 9). A desktop inkjet color printer (Epson Workforce 30) was used to print glucose test strips. The standard cyan, magenta and yellow ink cartridges were replaced with cartridges filled with GOx, chromogenic substrate (ABTS), and $MoS_2/Fe_3O_4$ solutions. Test strips were developed by printing layers of each solution in the form of a square on the paper. After dipping into glucose solution for 1 minute and heating at 45° C. for 10 minutes, the square block's color on the strip changed from colorless to green. The intensity of color was dependent on the concentration of glucose solution. It could be observed from the naked eye that the test strips allowed glucose detection as low as 12.5 mM or 225 mg/dL, which was sufficient to distinguish blood glucose concentration in healthy (3-8 mM) and diabetic persons (9-40 mM).[33] Therefore, the colorimetric detection of glucose from test strips made of $MoS_2/Fe_3O_4$ composites can be used for quick determination of glucose concentration. In addition to blood glucose detection, this is a powerful tool for non-invasive glucose detection using saliva, since direct correlation between saliva and blood glucose have been reported.[34-36] The strip can be used in developing world areas with low or no diagnostic resources. In an advanced version, a process may be used to digitize the results to be able to read on a portable device.

SUMMARY

In summary, a facile one-step scalable method to fabricate 2D/0D nanocomposites by exfoliating 2D materials via functionalized nanoparticles is reported here. $MoS_2/Fe_3O_4$ nanocomposites were developed and their peroxidase-like catalytic activity was explored to colorimetrically detect $H_2O_2$ and Glucose with LOD 1.5 µM and 25 µM. Glucose test strips were developed that changed their color in presence of glucose solutions as low as 225 mg/dL. $MoS_2/Fe_3O_4$ nanocomposites may be used for affordable, portable, and point-of-care diagnostics. A variety of 2D/0D nanocomposites may be formed by changing 2D materials and NPs.

REFERENCES

1. Li, X.; Shan, J. Y.; Zhang, W. Z.; Su, S.; Yuwen, L. H.; Wang, L. H. Recent Advances in Synthesis and Biomedical Applications of Two-Dimensional Transition Metal Dichalcogenide Nanosheets. *Small* 2017, 13.
2. Deng, D. H.; Novoselov, K. S.; Fu, Q.; Zheng, N. F.; Tian, Z. Q.; Bao, X. H. Catalysis with two-dimensional materials and their heterostructures. *Nat. Nanotechnol.* 2016, 11, 218-230.
3. Lv, R.; Robinson, J. A.; Schaak, R. E.; Sun, D.; Sun, Y. F.; Mallouk, T. E.; Terrones, M. Transition Metal Dichalcogenides and Beyond: Synthesis, Properties, and Applications of Single- and Few-Layer Nanosheets. *Acc. Chem. Res.* 2015, 48, 56-64.
4. Xu, M. S.; Liang, T.; Shi, M. M.; Chen, H. Z. Graphene-Like Two-Dimensional Materials. *Chem. Rev.* 2013, 113, 3766-3798.
5. Liu, T.; Shi, S. X.; Liang, C.; Shen, S. D.; Cheng, L.; Wang, C.; Song, X. J.; Goel, S.; Barnhart, T. E.; Cai, W. B.; Liu, Z. Iron Oxide Decorated $MoS_2$ Nanosheets with Double PEGylation for Chelator-Free Radio labeling and Multimodal Imaging Guided Photothermal Therapy. *ACS Nano* 2015, 9, 950-960.
6. Zhu, C. B.; Mu, X. K.; van Aken, P. A.; Maier, J.; Yu, Y. Fast Li Storage in $MoS_2$-Graphene-Carbon Nanotube Nanocomposites: Advantageous Functional Integration of 0D, 1D, and 2D Nanostructures. *Adv Energy Mater* 2015, 5.
7. Qu, Q. T.; Yang, S. B.; Feng, X. L. 2D Sandwich-like Sheets of Iron Oxide Grown on Graphene as High Energy Anode Material for Supercapacitors. *Adv. Mater.* 2011, 23, 5574-+.
8. Ahmad, R.; Srivastava, R.; Yadav, S.; Singh, D.; Gupta, G.; Chand, S.; Sapra, S. Functionalized Molybdenum Disulfide Nanosheets for 0D-2D Hybrid Nanostructures: Photoinduced Charge Transfer and Enhanced Photoresponse. *J Phys Chem Lett* 2017, 8, 1729-1738.
9. Kufer, D.; Nikitskiy, I.; Lasanta, T.; Navickaite, G.; Koppens, F. H. L.; Konstantatos, G. Hybrid 2D-0D $MoS_2$—PbS Quantum Dot Photodetectors. *Adv. Mater.* 2015, 27, 176-180.
10. Nicolosi, V.; Chhowalla, M.; Kanatzidis, M. G.; Strano, M. S.; Coleman, J. N. Liquid Exfoliation of Layered Materials. *Science* 2013, 340, 1420-+.
11. Joensen, P.; Frindt, R. F.; Morrison, S. R. Single-Layer Mos2. *Mater. Res. Bull.* 1986, 21, 457-461.
12. Yang, D.; Frindt, R. F. Li-intercalation and exfoliation of WS2. *J. Phys. Chem. Solids* 1996, 57, 1113-1116.
13. Sandoval, S. J.; Yang, D.; Frindt, R. F.; Irwin, J. C. Raman-Study and Lattice-Dynamics of Single Molecular Layers of Mos2. *Phys Rev B* 1991, 44, 3955-3962.
14. Coleman, J. N. Liquid Exfoliation of Defect-Free Graphene. *Acc. Chem. Res.* 2013, 46, 14-22.
15. Smith, R. J.; King, P. J.; Lotya, M.; Wirtz, C.; Khan, U.; De, S.; O'Neill, A.; Duesberg, G. S.; Grunlan, J. C.; Moriarty, G.; Chen, J.; Wang, J. Z.; Minett, A. I.; Nicolosi, V.; Coleman, J. N. Large-Scale Exfoliation of Inorganic Layered Compounds in Aqueous Surfactant Solutions. *Adv. Mater.* 2011, 23, 3944-+.
16. Wei, H.; Wang, E. Fe3O4 magnetic nanoparticles as peroxidase mimetics and their applications in $H_2O_2$ and glucose detection. *Anal. Chem.* 2008, 80, 2250-2254.
17. Song, Y. J.; Qu, K. G.; Zhao, C.; Ren, J. S.; Qu, X. G. Graphene Oxide: Intrinsic Peroxidase Catalytic Activity and Its Application to Glucose Detection. *Adv. Mater.* 2010, 22, 2206-2210.
18. Nandwana, V.; Ryoo, S. R.; Kanthala, S.; De, M.; Chou, S. S.; Prasad, P. V.; Dravid, V. P. Engineered Theranostic Magnetic Nanostructures: Role of Composition and Surface Coating on Magnetic Resonance Imaging Contrast and Thermal Activation. *ACS Appl. Mater. Interfaces* 2016, 8, 6953-6961.
19. Nandwana, V.; Ryoo, S. R.; Kanthala, S.; McMahon, K. M.; Rink, J. S.; Li, Y.; Venkatraman, S. S.; Thaxton, C. S.; Dravid, V. P. High-Density Lipoprotein-like Magnetic Nanostructures (HDL-MNS): Theranostic Agents for Cardiovascular Disease. *Chem. Mater.* 2017, 29, 2276-2282.
20. Poulin, S.; Franca, R.; Moreau-Belanger, L.; Sacher, E. Confirmation of X-ray Photoelectron Spectroscopy Peak Attributions of Nanoparticulate Iron Oxides, Using Symmetric Peak Component Line Shapes. *J. Phys. Chem. C* 2010, 114, 10711-10718.
21. Yamashita, T.; Hayes, P. Analysis of XPS spectra of Fe2+ and Fe3+ ions in oxide materials. *Appl. Surf. Sci.* 2008, 254, 2441-2449.
22. Wilson, D.; Langell, M. A. XPS analysis of oleylamine/oleic acid capped Fe3O4 nanoparticles as a function of temperature. *Appl. Surf. Sci.* 2014, 303, 6-13.
23. McCreary, K. M.; Hanbicki, A. T.; Robinson, J. T.; Cobas, E.; Culbertson, J. C.; Friedman, A. L.; Jernigan, G. G.; Jonker, B. T. Large-Area Synthesis of Continuous and Uniform MoS2 Monolayer Films on Graphene. *Adv. Funct. Mater.* 2014, 24, 6449-6454.
24. George, A. S.; Mutlu, Z.; Ionescu, R.; Wu, R. J.; Jeong, J. S.; Bay, H. H.; Chai, Y.; Mkhoyan, K. A.; Ozkan, M.; Ozkan, C. S. Wafer Scale Synthesis and High Resolution Structural Characterization of Atomically Thin MoS2 Layers. *Adv. Funct. Mater.* 2014, 24, 7461-7466.
25. Wang, S. S.; Wang, X. C.; Warner, J. H. All Chemical Vapor Deposition Growth of MoS2:h-BN Vertical van der Waals Heterostructures. *ACS Nano* 2015, 9, 5246-5254.

26. Li, H.; Zhang, Q.; Yap, C. C. R.; Tay, B. K.; Edwin, T. H. T.; Olivier, A.; Baillargeat, D. From Bulk to Monolayer MoS2: Evolution of Raman Scattering. *Adv. Funct. Mater.* 2012, 22, 1385-1390.

27. Gao, L. Z.; Zhuang, J.; Nie, L.; Zhang, J. B.; Zhang, Y.; Gu, N.; Wang, T. H.; Feng, J.; Yang, D. L.; Perrett, S.; Yan, X. Intrinsic peroxidase-like activity of ferromagnetic nanoparticles. *Nat. Nanotechnol.* 2007, 2, 577-583.

28. Hosoda, H.; Takasaki, W.; Oe, T.; Tsukamoto, R.; Nambara, T. Studies on Steroids 0.225. A Comparison of Chromogenic Substrates for Horseradish-Peroxidase as a Label in Steroid Enzyme-Immunoassay. *Chemical & Pharmaceutical Bulletin* 1986, 34, 4177-4182.

29. Chou, T. C.; Talalay, P. Simple Generalized Equation for Analysis of Multiple Inhibitions of Michaelis-Menten Kinetic Systems. *J. Biol. Chem.* 1977, 252, 6438-6442.

30. Dong, Y. L.; Zhang, H. G.; Rahman, Z. U.; Su, L.; Chen, X. J.; Hu, J.; Chen, X. G. Graphene oxide-Fe3O4 magnetic nanocomposites with peroxidase-like activity for colorimetric detection of glucose. *Nanoscale* 2012, 4, 3969-3976.

31. Park, S.; Boo, H.; Chung, T. D. Electrochemical non-enzymatic glucose sensors. *Anal. Chim. Acta* 2006, 556, 46-57.

32. Oliver, N. S.; Toumazou, C.; Cass, A. E. G.; Johnston, D. G. Glucose sensors: a review of current and emerging technology. *Diabetic Med* 2009, 26, 197-210.

33. Badugu, R.; Lakowicz, J. R.; Geddes, C. D. Noninvasive continuous monitoring of physiological glucose using a monosaccharide-sensing contact lens. *Anal. Chem.* 2004, 76, 610-618.

34. Soni, A.; Jha, S. K. A paper strip based non-invasive glucose biosensor for salivary analysis. *Biosensors & Bioelectronics* 2015, 67, 763-768.

35. Sashikumar, R.; Kalman, R. Salivary glucose levels and oral candidal carriage in type II diabetics. *Oral Surg Oral Med O* 2010, 109, 706-711.

36. Du, Y. Q.; Zhang, W. J.; Wang, M. L. Sensing of Salivary Glucose Using Nano-Structured Biosensors. *Biosensors-Basel* 2016, 6.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method of making a nanocomposite, the method comprising combining a first type of nanostructure with a bulk material in water or an aqueous solution, the first type of nanostructure functionalized with a functional group capable of undergoing van der Waals interactions with the bulk material, whereby the first type of nanostructure induces exfoliation of the bulk material to provide a second, different type of nanostructure therefrom while inducing association between the first and second types of nanostructures to form the nanocomposite, wherein the first type of nanostructure is selected from 0D nanostructures, 1D nanostructures, 2D nanostructures and combinations thereof, and the second, different type of nanostructure is a 2D nanostructure, and further wherein the nanocomposite comprises the first type of nanostructure distributed on exposed surfaces of the second, different type of nanostructure.

2. The method of claim 1, wherein the bulk material is unfunctionalized.

3. The method of claim 1, further comprising depositing the nanocomposite on a substrate to form a sensor.

4. The method of claim 1, wherein the first type of nanostructure is a 0D nanoparticle and the second type of nanostructure is a 2D nanosheet, and further wherein the nanocomposite comprises 0D nanoparticles distributed on the exposed surfaces of 2D nanosheets.

5. The method of claim 1, wherein the compositions of the first and second types of nanostructures are independently selected from noble metals, quantum dots, graphene, transition metal chalcogenides, transition metal oxides, nitrides, and combinations thereof.

6. The method of claim 1, wherein the functional group is selected from a thiol, a sulfate, a carboxylate, a cholate, a sulfonate, and trimethyl ammonium.

7. The method of claim 1, wherein the composition of the first type of nanostructure is a transition metal oxide and the composition of the bulk material and the second type of nanostructure is a transition metal chalcogenide.

8. The method of claim 7, further wherein the functional group is a thiol.

9. The method of claim 7, wherein the transition metal oxide is $Fe_3O_4$ and the transition metal chalcogenide is $MoS_2$.

10. The method of claim 9, further wherein the functional group is a thiol.

11. A method of making a nanocomposite, the method comprising combining a first type of nanostructure with a bulk material in water or an aqueous solution, the first type of nanostructure functionalized with a functional group capable of undergoing van der Waals interactions with the bulk material, whereby the first type of nanostructure induces exfoliation of the bulk material to provide a second, different type of nanostructure while inducing association between the first and second types of nanostructures to form the nanocomposite, further comprising depositing the nanocomposite on a substrate to form a sensor, and further comprising depositing a chromogenic material on the substrate, the chromogenic material capable of exhibiting a color change when oxidized.

12. A method of making a nanocomposite, the method comprising combining a first type of nanostructure with a bulk material in water or an aqueous solution, the first type of nanostructure functionalized with a functional group capable of undergoing van der Waals interactions with the bulk material, whereby the first type of nanostructure induces exfoliation of the bulk material to provide a second, different type of nanostructure while inducing association between the first and second types of nanostructures to form the nanocomposite, further comprising depositing the nanocomposite on a substrate to form a sensor, further comprising depositing a chromogenic material on the substrate, the chromogenic material capable of exhibiting a color change when oxidized, and further comprising depositing an oxidoreductase on the substrate.

13. The method of claim 12, wherein the oxidoreductase is glucose oxidase.

14. The method of claim 13, wherein the composition of the first type of nanostructure is a transition metal oxide and the composition of the bulk material and the second type of nanostructure is a transition metal chalcogenide.

15. The method of claim 14, wherein the transition metal oxide is $Fe_3O_4$ and the transition metal chalcogenide is $MoS_2$.

* * * * *